United States Patent
Yaver et al.

(10) Patent No.: US 7,910,804 B2
(45) Date of Patent: Mar. 22, 2011

(54) POLYPEPTIDES HAVING ALPHA-GLUCOSIDASE ACTIVITY AND POLYNUCLEOTIDES ENCODING SAME

(75) Inventors: Debbie Yaver, Davis, CA (US); Janine Lin, Davis, CA (US); Alexander Blinkovsky, Davis, CA (US); Kimberly Brown, Elk Grove, CA (US); Michael Rey, Davis, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 12/696,453

(22) Filed: Jan. 29, 2010

(65) Prior Publication Data

US 2010/0192260 A1 Jul. 29, 2010

Related U.S. Application Data

(62) Division of application No. 12/053,831, filed on Mar. 24, 2008, now Pat. No. 7,662,605, which is a division of application No. 11/176,864, filed on Jul. 6, 2005, now Pat. No. 7,368,271.

(60) Provisional application No. 60/586,103, filed on Jul. 6, 2004.

(51) Int. Cl.
| | |
|---|---|
| *A01H 9/00* | (2006.01) |
| *C12N 15/82* | (2006.01) |
| *C12N 9/24* | (2006.01) |
| *C12N 5/04* | (2006.01) |
| *C12N 1/20* | (2006.01) |
| *C12N 15/00* | (2006.01) |
| *C12P 21/06* | (2006.01) |
| *C07H 21/04* | (2006.01) |

(52) U.S. Cl. ........ 800/295; 800/278; 800/284; 435/200; 435/419; 435/69.1; 435/252.3; 435/252.33; 435/320.1; 536/23.1; 536/23.2; 536/23.7

(58) Field of Classification Search ................. 800/295, 800/278, 284; 435/200, 419, 69.1, 252.3, 435/252.33, 320.1; 536/23.1, 23.2, 23.7
See application file for complete search history.

(56) References Cited

U.S. PATENT DOCUMENTS

2004/0101591 A1 5/2004 Sato et al.

OTHER PUBLICATIONS

Rudick and Elbein, 1974, *Archives of Biochemistry and Biophysics* 1611: 281-290.
Olutiola, 1981, *Mycologia* 73: 1130.
Kato et al., 2002, *Appl. Environ. Microbiol.* 68: 1250-1256.
Rudick et al., 1979, *Archives of Biochemistry and Biophysics* 193: 509.
Leibowitz and Mechlinski, 1926, *Hoppe-Seyler's Zeitschrift für Physiologische Chemie* 154: 64.
Tanaka et al., 2002, Biosci. Biotechnol. Biochem. 66: 2415-2423.
Yamasaki et al., 1977, *Agricultural and Biological Chemistry* 41: 1553.
Flores-Carreon and Ruiz-Herrera, 1972, *Biochemica et Biophysica Acta* 258: 496.
Yamasaki et al., 1976, *Agricultural and Biological Chemistry* 40: 669.
Kato et al., Sequence Alignment Accession No. Q9C1S7 (TreEMBIrel) Jun. 1, 2001.
2000WO-US07781 (Berka et al.) database GenBank, US National Library of Medicine, (Bethesda, MD, USA) No. AAF 07600, Mar. 22, 2000 Sequence alignment.
Keshiri G. et al., Detection and differentiation between mycotoxigenic and non-mycotoxigenic strains of two Fusarium spp. Using volatile production profiles and hydrolytic enzymes., Appl. Microbiol., 2000, vol. 89, pp. 825-833.
Schmoll M., et al., Cloning of genes expressed early during cellulase induction in *Hypocrea jecorina* by a rapid subtraction hybridization approach. Fungal Genetics and Biology, 2004, vol. 41, pp. 877-887.
Yamasaki et al., 1977, *Agricultural and Biological Chemistry* 41: 1451.

*Primary Examiner* — Ganapathirama Raghu
(74) *Attorney, Agent, or Firm* — Robert L. Starnes

(57) ABSTRACT

The present invention relates to isolated polypeptides having alpha-glucosidase activity and isolated polynucleotides encoding the polypeptides. The invention also relates to nucleic acid constructs, vectors, and host cells comprising the polynucleotides as well as methods for producing and using the polypeptides.

20 Claims, 6 Drawing Sheets

```
            M  F  F     K  K  L  L     T  S  A     A  A  L     T  G  T  A     L  A  Q     S  K  A
   1    ATGTTCTTCA AGAAGCTGCT CACTTCCGCT GCAGCCCTCA CAGGCACTGC GCTTGCCCAG AGCAAGGCAG
         G  V  E  D     L  D  K     P  R  R     D  L  E     K  D  L     S  K  C     P  G  Y  K
  71    GCGTCGAAGA CCTCGACAAG CCCCGCAGAG ACCTTTTCGA AAAGGACCTC TCCAAGTGTC CCGGCTACAA
         A  T  K     H  W  E     T  R  S  G     F  Y  A     D  L  S     L  A  G  Q     A  C  D
 141    AGCCACAAAG CACTGGGAGA CCCGATCTGG CTTTTACGCT GACCTTTCCC TCGCGGGTCA GGCCTGTGAT
         V  Y  G     I  D  L  P     E  L  K     L  E  V     E  Y  Q  T     E  D  R     L  H  V
 211    GTCTACGGAA TCGATCTGCC TGAGCTGAAA CTTGAGGTTG AATATCAGAC CGAAGACCGA CTGCATGTCA
         K  I  L  D     T  N  N     T  V  Y     Q  V  P  D     D  V  F     P  R  P     G  L  G  Q
 281    AGATCTTGGA TACGAACAAC ACTCTTTACC AAGTCCCAGA TGACGTTTTC CCTCGTCCTG GGCTCGGACA
         W  A  S     P  K  N     S  R  L  K     F  D  F     K  A  D     P  F  S  F     T  V  S
 351    GTGGCCTTCA CCCAAAAACT CGAGGCTCAA GTTTGACTTC AAGGCGGATC CTTTCTCCTT CACCGTTTCC
         R  R  D     T  D  E  V     L  F  D     T  S  G     S  D  L  V     F  E  S     Q  Y  V
 421    AGGAGGGATA CCGATGAAGT GCTTTTTGAT ACCTCGGGCA GCGATCTTGT CTTTGAGAGT CAGTACGTCT
         Y  L  K  T     K  L  P     D  R  P     H  L  Y  G     L  G  E     H  S  D     P  F  M  L
 491    ATCTCAAGAC CAAGCTTCCC GATCGCCCTC ATCTACGGA TCTCGGCGAG CATAGCGATC CTTTCATGCT
         N  S  T     N  Y  T     R  T  I  Y     T  R  D     S  Y  G     T  P  K  G     Q  N  L
 561    GAACTCGACC AACTACACCC GCACTATCTA CACCCGCGAC TCATATGGTA CACCCAAGGG TCAAAACCTC
         Y  G  A     H  P  I  Y     F  D  H     R  E  K     G  T  H  G     V  F  L     L  N  S
 631    TATGGAGCTC ATCCCATCTA CTTCGATCAT CGGGAGAAGG GCACTCACGG TGTTTTCCTT CTCAACTCCA
         N  G  M  D     V  F  I     D  K  K     N  G  Q  Q     F  L  E     Y  N  I     I  G  G  V
 701    ACGGCATGGA CGTTTTCATC GATAAGAAGA ATGGCCAGCA GTTTTTGGAG TATAATATTA TTGGCGGTGT
         L  D  F     Y  F  V     A  G  P  S     P  R  D     V  A  K     Q  Y  A  E     I  T  T
 771    TCTCGACTTT TACTTCGTTG CTGGGCCATC GCCTCGTGAT GTCGCGAAGC AGTACGCCGA GATTACCACT
         L  P  L     M  T  P  Y     W  G  L     G  F  H     Q  C  R  Y     G  Y  R     D  V  Y
 841    CTACCCCTCA TGACGCCTTA CTGGGGTCTC GGTTTTCACC AGTGCCGATA CGGCTACCGT GATGTTTATG
         E  V  A  A     V  V  A     N  Y  S     A  A  G  I     P  L  E     T  M  W     T  D  I  D
 911    AGGTTGCTGC TGTTGTAGCC AACTATTCCG CTGCTGGAAT CCCACTCGAG ACGATGTGGA CAGATATTGA
         Y  M  D     R  R  R     I  F  T  I     D  P  E     R  F  P     A  D  K  Y     K  D  L
 981    CTACATGGAC CGTCGACGCA TCTTCACCAT TGATCCAGAG CGCTTCCCTG CAGACAAGTA CAAGGACCTT
         V  D  T     I  H  A  R     D  Q  K     Y  I  V     M  V  D  P     A  V  Y     D  M  E
1051    GTTGATACGA TCCATGCACG AGACCAGAAG TACATCGTCA TGGTTGACCC AGCCGTATAT GACATGGAAT
         S  N  P     A  L  D  S     G  L  E     Y  D  T  F     M  K  E     P  N  G     S  D  Y  R
1121    CTAATCCGGC CCTTGATTCA GGCCTCGAGT ACGACACTTT CATGAAAGAG CCCAACGGCT CCGACTACCG
         G  V  V     W  A  G     P  S  V  F     P  D  W     F  N  P     N  S  Q  K     Y  W  N
1191    AGGTGTTGTG TGGGCTGGAC CCAGTGTCTT CCCTGACTGG TTCAACCCCA ACTCACAAAA GTACTGGAAC
         E  L  F     A  N  F  F     D  G  E     N  G  P     D  I  D  G     L  W  I     D  M  N
1261    GAGCTCTTTG CCAATTTCTT CGATGGCGAG AACGGTCCTG ATATCGATGG TCTCTGGATT GATATGAATG
         E  P  A  N     F  F  N     R  P  Y     P  G  N  N     T  T  P     E  K  F     A  E  I  D
1331    AGCCTGCAAA CTTCTTCAAC CGTCCTTACC CTGGCAACAA CACCACTCCT GAGAAGTTCG CAGAGATTGA
         G  D  P     P  K  P     P  P  V  R     D  G  P     P  A  P     I  P  G  F     P  D  S
1401    TGGTGATCCC CCCAAGCCGC CTCCCGTCCG TGATGGTCCT CCTGCTCCTA TCCCTGGCTT CCCCGACAGT
         L  Q  P     A  S  S  R     L  N  T     R  E  S     V  S  I  A     K  T  T     I  H  K
1471    CTACAGCCTG CATCTTCTCG TCTTAACACG CGTGAGTCTG TTTCCATCGC CAAGACCACC ATCCACAAGC
         R  S  M  A     A  R  T     T  S  H     S  R  G  V     G  Q  W     A  T  K     K  H  W  G
1541    GCTCCATGGC AGCCCGCACA ACATCCCACA GCCGTGGCGT TGGACAGTGG GCTACCAAGA AGCACTGGGG
         Q  N  K     Y  G  R     P  G  S  S     W  P  N     G  K  K     T  G  S  G     C  G  P
1611    ACAGAACAAG TACGGCCGCC CTGGCTCCAG CTGGCCAAAT GGCAAGAAGA CCGGATCTGG TTGTGGCCCG
         N  E  C     K  G  L  P     N  R  E     L  I  Q     P  P  Y  M     I  Q  N     G  A  G
```

Fig. 1A

```
1681   AATGAGTGCA AGGGTCTTCC CAATCGAGAG CTCATCCAGC CTCCCTACAT GATCCAGAAC GGCGCGGGAC
        P  T  L  A   D  G  T    T  D  T    D  L  V  Q   S  G  D    Y  L  Q   Y  D  T  H
1751   CGACGCTTGC TGACGGCACT ACCGATACCG ATCTTGTGCA GAGCGGAGAT TACCTCCAGT ATGACACACA
        N  L  Y   G  A  Q    M  S  T  H   S  H  N    A  M  R   A  R  R  P    D  K  R
1821   CAACTTGTAC GGCGCTCAGA TGTCAACACA TTCGCACAAT GCCATGCGTG CTCGACGTCC CGACAAGCGC
        A  L  V   I  T  R  S   T  F  A    G  S   K  D  V  S   H  W  L    G  D  N
1891   GCTCTTGTTA TCACGCGTAG CACCTTTGCT GGTTCTGGCA AGGATGTCTC GCATTGGCTT GGTGACAACC
        L  S  I  W   D  Q  Y   R  F  S   I  G  Q   L  Q  F    A  S  I   Y  Q  I  P
1961   TCTCGATCTG GGATCAGTAC CGCTTTAGCA TTGGTCAGCT TCTCCAATTT GCATCCATCT ACCAAATTCC
        V  V  G   A  D  V    C  G  F  G   G  N  V   T  E  T    L  C  A  R   W  A  T
2031   TGTTGTTGGT GCCGATGTCT GTGGTTTCGG CGGTAACGTC ACTGAGACTC TATGCGCTAG ATGGGCTACG
        L  G  S   F  Y  T  F   F  R  N   H  N  E   I  T  A  A   S  Q  E   F  Y  R
2101   CTTGGAAGTT TCTACACTTT CTTCCGTAAC CACAACGAGA TCACTGCTGC ATCACAAGAA TTCTACCGCT
        W  P  K  V   A  E  A   R  T    G  I  A  I   R  Y  K   L  L  D   Y  I  Y  T
2171   GGCCCAAGGT CGCCGAGGCA GCCCGTACTG GTATCGCCAT TCGTTACAAG CTCCTCGATT ACATCTACAC
        A  I  Y   K  Q  N    Q  T  G  T    P  T  L   N  P  L    F  F  N  Y    P  N  D
2241   TGCCATTTAC AAGCAGAACC AGACAGGCAC CCCTACTCTC AACCCTCTGT TCTTCAACTA CCCCAACGAC
        K  N  T   Y  S  I  D   L  Q  F    F  Y  G   D  G  I  L   V  S  P   V  T  K
2311   AAGAACACAT ACTCCATCGA CCTTCAGTTC TTTTATGGTG ATGGCATCCT CGTCAGCCCT GTTACAAAGG
        E  N  S  T   E  L  E   Y  Y  L    P  D  D  I   F  Y  E   W  S  T    G  K  P  V
2381   AGAACAGTAC TGAGTTGGAA TATTACCTCC CTGATGACAT TTTCTACGAG TGGTCCACCG GAAAGCCTGT
        R  G  T    G  S  Y   E  S  A  E   V  E  L    T  D  I   M  V  H  Y   K  G  G
2451   TCGTGGTACT GGTTCATATG AGTCTGCAGA GGTTGAGCTC ACTGATATCA TGGTTCATTA CAAGGGTGGC
        I  I  Y   P  Q  R  V   D  S  A   N  T  T    T  A  L  R   K  K  G   F  N  L
2521   ATCATCTACC CCCAGCGTGT CGACAGTGCC AACACTACCA CCGCTCTCCG CAAGAAGGGT TTCAACCTTG
        V  I  A  P   G  L  N   G  K  A    S  G  S  L   Y  L  D   D  G  E    S  V  V  Q
2591   TTATTGCACC CGGTCTGAAC GGTAAGGCTT CTGGATCTTT GTACCTCGAC GATGGAGAGT CTGTCGTCCA
        D  A  V   S  E  I    D  F  T  Y   T  K  G   K  L  S    M  G  G  S    F  E  Y
2661   GGACGCTGTA TCCGAGATTG ACTTCACTTA CACCAAGGGC AAGCTGAGTA TGGGTGGAAG CTTTGAGTAC
        D  A  G   V  K  I  E   T  I  T    I  L  G   V  E  K  Q   P  K  G   T  D  H  ]
2731   GATGCCGGTG TCAAGATTGA GACGATCACC ATTCTTGGTG TTGAAAAGCA GCCCAAGGGC ACCGATCATG
        A  E  Y  D   S  E  N   K  K  L    I  F  A  A   D  V  P   L  T  K   K  C  Y  V
2801   CAGAGTATGA CTCTGAGAAC AAGAAGCTGA TCTTTGCGGC GGATGTACCT TGACGAAGA AGTGTTATGT
        D  L  F  *
2871   GGATCTCTTC TGA
```

POLYPEPTIDES HAVING ALPHA-GLUCOSIDASE ACTIVITY AND POLYNUCLEOTIDES ENCODING SAME

CROSS-REFERENCE TO RELATED APPLICATIONS

This application is a divisional of U.S. application Ser. No. 12/053,831, filed Mar. 24, 2008, now U.S. Pat. No. 7,622,605, which is a divisional of U.S. application Ser. No. 11/176,864, filed Jul. 6, 2005, now U.S. Pat. No. 7,368,271, which claims priority from U.S. Provisional Application Ser. No. 60/586,103, filed Jul. 6, 2004, which applications are fully incorporated herein by reference.

BACKGROUND OF THE INVENTION

1. Field of the Invention

The present invention relates to isolated polypeptides having alpha-glucosidase activity and isolated polynucleotides encoding the polypeptides. The invention also relates to nucleic acid constructs, vectors, and host cells comprising the polynucleotides as well as methods for producing and using the polypeptides.

2. Description of the Related Art

Several enzymes are involved in the degradation of starch. The enzymes include alpha-amylase, beta-amylase, amyloglucosidase, pullulanase, isoamylase, alpha-glucosidase, and cylcodextrin glycosyltransferase.

Alpha-glucosidases (EC 3.2.1.20) hydrolyze terminal, non-reducing alpha-1,4-linked glucose residues in various substrates, releasing glucose. They degrade disaccharides and oligosaccharides quickly while polysaccharides are attacked slowly if at all. Maltose, maltose derivatives, sucrose, aryl-alpha-glucosides, and alkyl-alpha-glucosides can act as substrates.

Other filamentous fungi have been reported to produce alpha-glucosidases such as *Aspergillus fumigatus* (Rudick and Elbein, 1974, *Archives of Biochemistry and Biophysics* 1611: 281-290), *Aspergillus flavus* (Olutiola, 1981, *Mycologia* 73: 1130), *Aspergillus nidulans* (Kato et al., 2002, *Appl. Environ. Microbiol.* 68: 1250-1256), *Aspergillus niger* (Rudick et al., 1979, *Archives of Biochemistry and Biophysics* 193: 509), *Aspergillus oryzae* (Leibowitz and Mechlinski, 1926, *Hoppe-Seyler's Zeitschrift für Physiologische Chemie* 154:64), *Mortierella alliacea* (Tanaka et al., 2002, *Biosci. Biotechnol. Biochem.* 66: 2415-2423), *Mucor javanicus* (Yamasaki et al., 1978, *Berichte des Ohara Instituts für Landwirtschaftliche Biologie* 17: 123), *Mucor rouxii* (Flores-Carreon and Ruiz-Herrera, 1972, *Biochemica et Biophysica Acta* 258: 496), *Penicillium pupurogenum* (Yamasaki et al., 1976, *Agricultural and Biological Chemistry* 40: 669), and *Penicillium oxalicum* (Yamasaki et al., 1977, *Agricultural and Biological Chemistry* 41: 1451).

Alpha-glucosidases can be used in combination with other starch-degrading enzymes, e.g., alpha-amylase, to achieve complete hydrolysis of starch in industrial applications where conversion to fermentable sugars is desirable. Consequently, there is a need in the art for alternative alpha-glucosidases with improved properties such as pH optimum, temperature optimum, and thermostability.

It is an object of the present invention to provide polypeptides having alpha-glucosidase activity and polynucleotides encoding the polypeptides.

SUMMARY OF THE INVENTION

The present invention relates to isolated polypeptides having alpha-glucosidase activity selected from the group consisting of:

(a) a polypeptide having an amino acid sequence which has at least 85% identity with amino acids 21 to 960 of SEQ ID NO: 2;

(b) a polypeptide which is encoded by a nucleotide sequence which hybridizes under at least high stringency conditions with (i) nucleotides 61 to 2880 of SEQ ID NO: 1, (ii) the genomic DNA sequence comprising nucleotides 61 to 2880 of SEQ ID NO: 1, or (iii) a complementary strand of (i) or (ii); and (c) a variant comprising a conservative substitution, deletion, and/or insertion of one or more amino acids of amino acids 21 to 960 of SEQ ID NO: 2.

The present invention also relates to isolated polynucleotides encoding polypeptides having alpha-glucosidase activity, selected from the group consisting of:

(a) a polynucleotide encoding a polypeptide having an amino acid sequence which has at least 85% identity with amino acids 21 to 960 of SEQ ID NO: 2;

(b) a polynucleotide having at least 85% identity with nucleotides 61 to 2880 of SEQ ID NO: 1; and (c) a polynucleotide which hybridizes under at least high stringency conditions with (i) nucleotides 61 to 2880 of SEQ ID NO: 1, (ii) the genomic DNA sequence comprising nucleotides 61 to 2880 of SEQ ID NO: 1, or (iii) a complementary strand of (i) or (ii).

The present invention also relates to nucleic acid constructs, recombinant expression vectors, and recombinant host cells comprising the polynucleotides.

The present invention also relates to methods for producing such polypeptides having alpha-glucosidase activity comprising (a) cultivating a recombinant host cell comprising a nucleic acid construct comprising a polynucleotide encoding the polypeptide under conditions conducive for production of the polypeptide; and (b) recovering the polypeptide.

The present invention also relates to methods of using the polypeptides.

The present invention further relates to nucleic acid constructs comprising a gene encoding a protein, wherein the gene is operably linked to a nucleotide sequence encoding a signal peptide consisting of nucleotides 1 to 60 of SEQ ID NO: 1, wherein the gene is foreign to the first and second nucleotide sequences.

BRIEF DESCRIPTION OF THE FIGURES

FIGS. 1A and 1B show the cDNA sequence and the deduced amino acid sequence of a *Fusarium venenatum* alpha-glucosidase (SEQ ID NOs: 1 and 2, respectively).

DEFINITIONS

Figure 2:
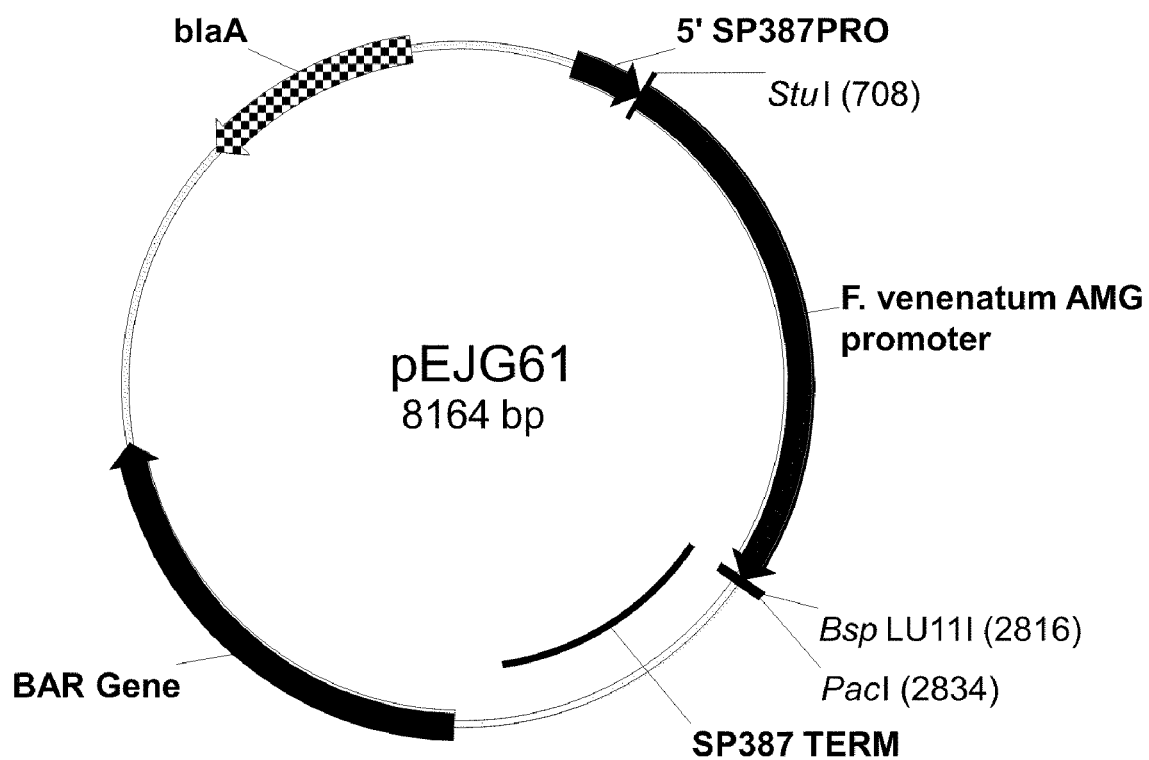
FIG. 2 shows a restriction map of pEJG61.

Alpha-glucosidase activity: The term "alpha-glucosidase activity" is defined herein as an alpha-D-glucoside glucohydrolase activity (E.C. 3.2.1.20) which catalyzes the exohydrolysis of terminal, non-reducing 1,4-linked alpha-D-glucose residues with the release of alpha-D-glucose. Natural substrates of the enzyme activity include, for example, maltose, maltotriose, maltotetraose, maltopentaose, starch (soluble), amylose, amylopectin, isomaltose, Kojibiose, sucrose, nigerose, turanose, melizitose, and glycogen. For purposes of the present invention, alpha-glucosidase activity is determined with maltose as substrate in 0.1 M sodium acetate buffer pH 4.3 at 25° C. One unit of alpha-glucosidase activity is defined as 1.0 mmole of glucose produced per minute at 25° C., pH 4.3 from maltose as substrate in sodium acetate buffer.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the alpha-glucosidase activity of the polypeptide consisting of the amino acid sequence shown as amino acids 21 to 960 of SEQ ID NO: 2.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively or recombinantly associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Identity: The relatedness between two amino acid sequences or between two nucleotide sequences is described by the parameter "identity".

For purposes of the present invention, the degree of identity between two amino acid sequences is determined by the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

For purposes of the present invention, the degree of identity between two nucleotide sequences is determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

Polypeptide Fragment The term "polypeptide fragment" is defined herein as a polypeptide having one or more amino acids deleted from the amino and/or carboxyl terminus of SEQ ID NO: 2 or a homologous sequence thereof, wherein the fragment has alpha-glucosidase activity. Preferably, a fragment contains at least 790 amino acid residues, more preferably at least 840 amino acid residues, and most preferably at least 890 amino acid residues of SEQ ID NO: 2.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively or recombinantly associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

Subsequence: The term "subsequence" is defined herein as a nucleotide sequence having one or more nucleotides deleted from the 5' and/or 3' end of SEQ ID NO: 1 or a homologous sequence thereof, wherein the subsequence encodes a polypeptide fragment having alpha-glucosidase activity. Preferably, a subsequence contains at least 2370 nucleotides, more preferably at least 2520 nucleotides, and most preferably at least 2670 nucleotides.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct comprising a polynucleotide of the present invention.

Modification: The term "modification" means herein any chemical modification of the polypeptide consisting of the amino acids 21 to 960 of SEQ ID NO: 2 or a homologous sequence thereof, as well as genetic manipulation of the DNA encoding that polypeptide. The modification can be substitutions, deletions and/or insertions of one or more amino acids as well as replacements of one or more amino acid side chains.

Artificial variant: When used herein, the term "artificial variant" means a polypeptide having alpha-glucosidase activity produced by an organism expressing a modified nucleotide sequence of SEQ ID NO: 1. The modified nucleotide sequence is obtained through human intervention by modification of the nucleotide sequence disclosed in SEQ ID NO: 1.

DETAILED DESCRIPTION OF THE INVENTION

Polypeptides Having Alpha-Glucosidase Activity

In a first aspect, the present invention relates to isolated polypeptides having an amino acid sequence which has a degree of identity to amino acids 21 to 960 of SEQ ID NO: 2 (i.e., the mature polypeptide) of at least 85%, preferably at least 90%, more preferably at least 95%, and most preferably at least 97%, which have alpha-glucosidase activity (hereinafter "homologous polypeptides"). In a preferred aspect, the homologous polypeptides have an amino acid sequence which differs by ten amino acids, preferably by five amino acids, more preferably by four amino acids, even more preferably by three amino acids, most preferably by two amino acids, and even most preferably by one amino acid from amino acids 21 to 960 of SEQ ID NO: 2.

A polypeptide of the present invention preferably comprises the amino acid sequence of SEQ ID NO: 2 or an allelic variant thereof; or a fragment thereof that has alpha-glucosidase activity. In a preferred aspect, a polypeptide comprises the amino acid sequence of SEQ ID NO: 2. In another preferred aspect, a polypeptide comprises amino acids 21 to 960 of SEQ ID NO: 2, or an allelic variant thereof; or a fragment thereof that has alpha-glucosidase activity. In another preferred aspect, a polypeptide comprises amino acids 21 to 960 of SEQ ID NO: 2. In another preferred aspect, a polypeptide consists of the amino acid sequence of SEQ ID NO: 2 or an allelic variant thereof; or a fragment thereof that has alpha-glucosidase activity. In another preferred aspect, a polypeptide consists of the amino acid sequence of SEQ ID NO: 2. In another preferred aspect, a polypeptide consists of amino acids 21 to 960 of SEQ ID NO: 2 or an allelic variant thereof; or a fragment thereof that has alpha-glucosidase activity. In another preferred aspect, a polypeptide consists of amino acids 21 to 960 of SEQ ID NO: 2.

In a second aspect, the present invention relates to isolated polypeptides having alpha-glucosidase activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) nucleotides 61 to 2880 of SEQ ID NO: 1, (ii) the genomic DNA sequence comprising nucleotides 61 to 2880 of SEQ ID NO: 1, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual,* 2d edition, Cold Spring Harbor, N.Y.). A subsequence of SEQ ID NO: 1 contains at least 100 contiguous nucleotides or preferably at least 200 continguous nucleotides. Moreover, the subsequence may encode a polypeptide fragment which has alpha-glucosidase activity.

The nucleotide sequence of SEQ ID NO: 1 or a subsequence thereof, as well as the amino acid sequence of SEQ ID NO: 2 or a fragment thereof, may be used to design a nucleic acid probe to identify and clone DNA encoding polypeptides having alpha-glucosidase activity from strains of different genera or species according to methods well known in the art. In particular, such probes can be used for hybridization with the genomic DNA or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other organisms may, therefore, be screened for DNA which hybridizes with the probes described above and which encodes a polypeptide having alpha-glucosidase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1 or a subsequence thereof, the carrier material is used in a Southern blot.

For purposes of the present invention, hybridization indicates that the nucleotide sequence hybridizes to a labeled nucleic acid probe corresponding to the nucleotide sequence shown in SEQ ID NO: 1, its complementary strand, or a subsequence thereof, under very low to very high stringency conditions. Molecules to which the nucleic acid probe hybridizes under these conditions can be detected using, for example, X-ray film.

In a preferred aspect, the nucleic acid probe is a polynucleotide sequence which encodes the polypeptide of SEQ ID NO: 2, or a subsequence thereof. In another preferred aspect, the nucleic acid probe is SEQ ID NO: 1. In another preferred aspect, the nucleic acid probe is the mature polypeptide coding region of SEQ ID NO: 1. In another preferred aspect, the nucleic acid probe is the polynucleotide sequence contained in plasmid pFD11F2 which is contained in *E. coli* NRRL B-30753, wherein the polynucleotide sequence thereof encodes a polypeptide having alpha-glucosidase activity. In another preferred aspect, the nucleic acid probe is the mature polypeptide coding region contained in plasmid pFD11F2 which is contained in *E. coli* NRRL B-30753.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$, using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polypeptides having alpha-glucosidase activity having the following physicochemical properties: a pH optimum in the range of about 4.5 to about 6.0, preferably about 4.7 to about 5.7, more preferably about 4.8 to about 5.5, most preferably about 5.0 to about 5.3, and even most preferably at pH 5.0 in 50 mM sodium acetate buffer/50 mM potassium phosphate buffer at 37° C., and thermostability up to about 65° C. (approximately 77% residual activity) in 50 mM sodium acetate pH 5.0 for 5 minutes.

In a fourth aspect, the present invention relates to artificial variants comprising a conservative substitution, deletion, and/or insertion of one or more amino acids of SEQ ID NO: 2 or the mature polypeptide thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for biological activity (i.e., alpha-glucosidase activity) to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochem. 30:10832-10837; U.S. Pat. No. 5,223,409; WO 92/06204), and region-directed mutagenesis (Derbyshire et al., 1986, Gene 46: 145; Ner et al., 1988, DNA 7:127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of amino acids 21 to 960 of SEQ ID NO: 2 is 10, preferably 9, more preferably 8, more preferably 7, more preferably at most 6, more preferably at most 5, more preferably 4, even more preferably 3, most preferably 2, and even most preferably 1.

Sources of Polypeptides Having Alpha-Glucosidase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a cell in which the nucleotide sequence from the source has been inserted. In a preferred aspect, the polypeptide obtained from a given source is secreted extracellularly.

A polypeptide of the present invention may be a bacterial polypeptide. For example, the polypeptide may be a gram positive bacterial polypeptide such as a Bacillus polypeptide, e.g., a Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis, or Bacillus thuringiensis polypeptide; or a Streptomyces polypeptide, e.g., a Streptomyces lividans or Streptomyces murinus polypeptide; or a gram negative bacterial polypeptide, e.g., an E. coli or a Pseudomonas sp. polypeptide.

A polypeptide of the present invention may also be a fungal polypeptide, and more preferably a yeast polypeptide such as a Candida, Kluyveromyces, Pichia, Saccharomyces, Schizosaccharomyces, or Yarrowia polypeptide; or more preferably a filamentous fungal polypeptide such as an Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium, or Trichoderma polypeptide.

In a preferred aspect, the polypeptide is a Saccharomyces carlsbergensis, Saccharomyces cerevisiae, Saccharomyces diastaticus, Saccharomyces douglasii, Saccharomyces kluyveri, Saccharomyces norbensis, or Saccharomyces oviformis polypeptide having alpha-glucosidase activity.

In another preferred aspect, the polypeptide is an Aspergillus aculeatus, Aspergillus awamori, Aspergillus fumigatus, Aspergillus foetidus, Aspergillus japonicus, Aspergillus nidulans, Aspergillus niger, Aspergillus oryzae, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei, or Trichoderma viride polypeptide having alpha-glucosidase activity.

In another preferred aspect, the polypeptide is an Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum polypeptide having alpha-glucosidase activity.

In a more preferred aspect, the polypeptide is a Fusarium venenatum polypeptide, and most preferably a Fusarium venenatum NRRL 30747 polypeptide, e.g., the polypeptide of SEQ ID NO: 2 or amino acids 21 to 960 of SEQ ID NO: 2.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic DNA or cDNA library of another microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides

The present invention also relates to isolated polynucleotides having a nucleotide sequence which encode a polypeptide of the present invention. In a preferred aspect, the nucleotide sequence is set forth in SEQ ID NO: 1. In another more preferred aspect, the nucleotide sequence is the sequence contained in plasmid pFD11F2 which is contained in *E. coli* NRRL B-30753. In another preferred aspect, the nucleotide sequence is the mature polypeptide coding region of SEQ ID NO: 1. In another more preferred aspect, the nucleotide sequence is the mature polypeptide coding region contained in plasmid pFD11F2 which is contained in *E. coli* NRRL B-30753. The present invention also encompasses nucleotide sequences which encode a polypeptide having the amino acid sequence of SEQ ID NO: 2 or the mature polypeptide thereof, which differ from SEQ ID NO: 1 by virtue of the degeneracy of the genetic code. The present invention also relates to subsequences of SEQ ID NO: 1 which encode fragments of SEQ ID NO: 2 that have alpha-glucosidase activity.

The present invention also relates to mutant polunucleotides comprising at least one mutation in the mature polypeptide coding sequence of SEQ ID NO: 1, in which the mutant nucleotide sequence encodes a polypeptide which consists of amino acids 21 to 960 of SEQ ID NO: 2.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a cell of *Aspergillus*, or another or related organism and thus, for example, may be an allelic or species variant of the polypeptide encoding region of the nucleotide sequence.

The present invention also relates to polynucleotides having nucleotide sequences which have a degree of identity to the mature polypeptide coding sequence of SEQ ID NO: 1 (i.e., nucleotides 142 to 2943) of at least 85%, preferably at least 90%, more preferably at least 95%, and most preferably at least 97% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the polypeptide encoding region of SEQ ID NO: 1, e.g., a subsequence thereof, and/or by introduction of nucleotide substitutions which do not give rise to another amino acid sequence of the polypeptide encoded by the nucleotide sequence, but which correspond to the codon usage of the host organism intended for production of the enzyme, or by introduction of nucleotide substitutions which may give rise to a different amino acid sequence. See, e.g., Ford et al., 1991, *Protein Expression and Purification* 2: 95-107 for a general description of nucleotide substitution.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for alpha-glucosidase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

The present invention also relates to isolated polynucleotides encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) nucleotides 61 to 2880 of SEQ ID NO: 1, (ii) the genomic DNA sequence comprising nucleotides 61 to 2880 of SEQ ID NO: 1, or (iii) a complementary strand of (i) or (ii); or allelic variants and subsequences thereof (Sambrook et al., 1989, supra), as defined herein.

The present invention also relates to isolated polynucleotides obtained by (a) hybridizing a population of DNA under very low, low, medium, medium-high, high, or very high stringency conditions with (i) nucleotides 61 to 2880 of SEQ ID NO: 1, (ii) the genomic DNA sequence comprising nucleotides 61 to 2880 of SEQ ID NO: 1, or (iii) a complementary strand of (i) or (ii); and (b) isolating the hybridizing polynucleotide, which encodes a polypeptide having alpha-glucosidase activity.

Nucleic Acid Constructs

The present invention also relates to nucleic acid constructs comprising an isolated polynucleotide of the present invention operably linked to one or more control sequences which direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (VIIIa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1,ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

In a preferred aspect, the signal peptide coding region is nucleotides 1 to 141 of SEQ ID NO: 1 which encode amino acids 1 to 20 of SEQ ID NO: 2.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus, Bacillus licheniformis, Bacillus stearothermophilus,* or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, Soc. *App. Bacteriol. Symposium Series* No. 9, 1980).

In an even more preferred aspect, the yeast host cell is a *Candida, Hansenula, Kluyveromyces, Pichia, Saccharomyces, Schizosaccharomyces,* or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans,*

*Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium* trichothecioides, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology, Volume* 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention, comprising (a) cultivating a cell, which in its wild-type form is capable of producing the polypeptide, under conditions conducive for production of the polypeptide; and (b) recovering the polypeptide. Preferably, the cell is of the genus *Fusarium*, and more preferably *Fusarium venenatum*.

The present invention also relates to methods for producing a polypeptide of the present invention, comprising (a) cultivating a host cell under conditions conducive for production of the polypeptide; and (b) recovering the polypeptide.

The present invention also relates to methods for producing a polypeptide of the present invention, comprising (a) cultivating a host cell under conditions conducive for production of the polypeptide, wherein the host cell comprises a mutant nucleotide sequence having at least one mutation in the mature polypeptide coding region of SEQ ID NO: 1, wherein the mutant nucleotide sequence encodes a polypeptide which consists of amino acids 21 to 960 of SEQ ID NO: 2, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Plants

The present invention also relates to a transgenic plant, plant part, or plant cell which has been transformed with a nucleotide sequence encoding a polypeptide having alpha-glucosidase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more expression constructs encoding a polypeptide of the present invention into the plant host genome and propagating the resulting modified plant or plant cell into a transgenic plant or plant cell.

The expression construct is conveniently a nucleic acid construct which comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron which is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods for producing a polypeptide of the present invention comprising (a) cultivating a transgenic plant or a plant cell comprising a polynucleotide encoding a polypeptide having alpha-glucosidase activity of the present invention under conditions conducive for production of the polypeptide; and (b) recovering the polypeptide.

Removal or Reduction of Alpha-Glucosidase Activity

The present invention also relates to methods for producing a mutant of a parent cell, which comprises disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence which is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred embodiment, the nucleotide sequence is disrupted with a selectable marker such as those described herein.

Alternatively, modification or inactivation of the nucleotide sequence may be performed by established anti-sense techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell which comprises a disruption or deletion of a nucleotide sequence encoding the polypeptide or a control sequence thereof, which results in the mutant cell producing less of the polypeptide than the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of alpha-glucosidase activity by fermentation of a cell which produces both a polypeptide of the present invention as well as the protein product of interest by adding an effective amount of an agent capable of inhibiting alpha-glucosidase activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of alpha-glucosidase activity by cultivating the cell under conditions permitting the expression of the product, subjecting the resultant culture broth to a combined pH and temperature treatment so as to reduce the alpha-glucosidase activity substantially, and recovering the product from the culture broth. Alternatively, the combined pH and temperature treatment may be performed on an enzyme preparation recovered from the culture broth. The combined pH and temperature treatment may optionally be used in combination with a treatment with a alpha-glucosidase inhibitor.

In accordance with this aspect of the invention, it is possible to remove at least 60%, preferably at least 75%, more preferably at least 85%, still more preferably at least 95%, and most preferably at least 99% of the alpha-glucosidase activity. Complete removal of alpha-glucosidase activity may be obtained by use of this method.

The combined pH and temperature treatment is preferably carried out at a pH in the range of 4-5 and a temperature in the range of 70-80° C. for a sufficient period of time to attain the desired effect, where typically, 30 to 60 minutes is sufficient.

The methods used for cultivation and purification of the product of interest may be performed by methods known in the art.

The methods of the present invention for producing an essentially alpha-glucosidase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The alpha-glucosidase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from alpha-glucosidase activity which is produced by a method of the present invention.

Compositions

The present invention also relates to compositions comprising a polypeptide of the present invention. Preferably, the compositions are enriched in such a polypeptide. The term "enriched" indicates that the alpha-glucosidase activity of the composition has been increased, e.g., with an enrichment factor of 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus, Aspergillus awamori, Aspergillus fumigatus, Aspergillus foetidus, Aspergillus japonicus, Aspergillus nidulans, Aspergillus niger*, or *Aspergillus oryzae; Fusarium*, preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides*, or *Fusarium venenatum; Humicola*, preferably *Humicola insolens* or *Humicola lanuginosa*; or *Trichoderma*, preferably *Trichoderma harzianum, Trichoderma koningii, Trichoderma longibrachiatum, Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having alpha-glucosidase activity.

The polypeptides of the present invention may be used in the production of alcohol from cereal grains according to DE 2944483.

The polypeptides of the present invention may also be used to produce fermented malt drinks, e.g., (low-caloric) beer, according to WO 2002/55652 (published U.S. Patent Application 20040101591). Fermented malt beverages with reinforced filling taste and fullness of mouthfeel can be produced by addition of a polypeptide having alpha-glucosidase activity prior to heat treatment in a wort production process in the course of manufacturing fermented malt beverages. Low-calorie beers can be manufactured in which a polypeptide having alpha-glucosidase activity is added in the fermentation process in the brewing of beer. Production of acetic acid can be reduced by addition of a polypeptide having alpha-glucosidase activity in the fermentation process in the high gravity brewing of beer.

In manufacturing beers, starch derived from ingredients including malt is hydrolyzed by hydrolases (e.g., alpha-amylase, beta-amylase) and fermentable sugars such as glucose, maltose, and maltotriose, which a brewer's yeast can metabolize, oligosaccharides larger than maltotetraose, and dextrin are produced. The fermentable sugars are then metabolized by brewer's yeast (or other yeast) and converted to various components of beer such as alcohol. Oligosaccharides larger than maltotetraose and dextrin may remain in the beer without being metabolized and may participate in filling taste and fullness of mouthfeel of the beverages.

In a preferred aspect, the method relates to producing a fermented malt beverage, wherein a polypeptide having alpha-glucosidase activity of the present invention is added prior to heat treatment of wort in a wort production process for manufacturing a fermented malt beverage. In another more preferred aspect, the amount of the polypeptide having alpha-glucosidase activity used is 50-400 ppm per the amount of the malt. In another preferred aspect, the polypeptide having alpha-glucosidase activity is added simultaneously with ground malt. In another preferred aspect, the polypeptide having alpha-glucosidase activity is added to the mash prior to the heat treatment in the wort production process. In another preferred aspect, the polypeptide having alpha-glucosidase activity is added in the malting process. In another preferred aspect, only malt is used as an ingredient. In another preferred aspect, malt and adjuncts are used as sugar ingredients.

In another preferred aspect, the method relates to producing a beer, wherein a polypeptide having alpha-glucosidase activity of the present invention is added to the fermentation process in the brewing of the beer. In a more preferred aspect, the beer is a low-calorie beer or light beer. In another preferred aspect, the addition of the polypeptide having alpha-glucosidase activity reduces acetic acid production. In another more preferred aspect, the concentration of original extract of wort is over 10 and not more than 30 weight %. In another more preferred aspect, the amount of the polypeptide having alpha-glucosidase activity used is 50-400 ppm per the amount of the malt.

Signal Peptide

The present invention also relates to nucleic acid constructs comprising a gene encoding a protein operably linked to a nucleotide sequence consisting of nucleotides 61 to 2880 of SEQ ID NO: 1 encoding a signal peptide consisting of amino acids 1 to 20 of SEQ ID NO: 2, wherein the gene is foreign to the nucleotide sequence.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples which should not be construed as limiting the scope of the invention.

EXAMPLES

Materials

Chemicals used as buffers and substrates were commercial products of at least reagent grade.
Fungal Strains
*Fusarium venenatum* strain WTY842-1-11 (Δtri5, amdS$^+$) was used for expression of the *Fusarium venenatum* GH31 alpha-glucosidase gene.
Media and Solutions
RA Sporulation medium was composed per liter of 1 g of glucose, 50 g of succinic acid, 12.1 g of NaNO$_3$, and 20 ml of 50× Vogel's salts (no C, no N).

50× Vogel's salts (no C, no N) was composed per liter of 250 g of KH$_2$PO$_4$, 10 g of MgSO$_4$.7H$_2$O, 5 g of CaCl$_2$.2H$_2$O, 2.5 ml of biotin solution, and 5 ml of Vogel's trace elements.

50× Vogel's trace elements solution was composed per liter of 50 g of citric acid, 50 g of ZnSO$_4$.7H$_2$O, 10 g of Fe(NH$_4$)$_2$(SO$_4$)$_2$.6H$_2$O, 2.5 g of CuSO$_4$.5H$_2$O, 0.5 g of MnSO$_4$.H$_2$O, 0.5 g of H$_3$BO$_3$, and 0.5 g of Na$_2$MoO$_4$.2H$_2$O.

YPG medium was composed per liter of 1% yeast extract, 2% bactopeptone, and 5% glucose.

Vogel's NO$_3$ Regeneration Low-Melt medium was composed per liter of 20 ml of 50× Vogels solution with 25 mM NaNO$_3$ stock, 0.8 M sucrose and 1.5% low melting agarose (Sigma Chemical Company, St. Louis, Mo.).

50× Vogels solution with 25 mM NaNO$_3$ stock was composed of per liter of 125 g of sodium citrate, 250 g of KH$_2$PO$_4$, 106.25 g of NaNO$_3$, 10 g of MgSO$_4$.7H$_2$O, 5 g of CaCl$_2$.2H$_2$O, 2.5 ml of biotin solution, and 5 ml of 50× Vogels trace element solution.

Vogel's NO$_3$+BASTA (6 mg/ml) medium was composed per liter of 25 g of sucrose, 25 g of Noble agar, 20 ml of 50× Vogel's salts with 25 mM NaNO$_3$ stock, and 6 g of BASTA per liter.

M400 medium was composed per liter of 50 g of maltodextrin, 2 g of MgSO$_4$.7H$_2$O, 2 g of KH$_2$PO$_4$, 4 g of citric acid, 8 g of yeast extract, 2 g of urea, 0.5 g of CaCl$_2$, and 0.5 ml of AMG trace metals solution.

AMG trace metals solution was composed per liter of 14.3 g of ZnSO$_4$.7H$_2$O, 2.5 g of CuSO$_4$.5H$_2$O, 0.5 g of NiCl$_2$.6H$_2$O, 13.8 g of FeSO$_4$.7H$_2$O, 8.5 g of MnSO$_4$.H$_2$O, and 3 g of citric acid.

50× Vogel's salts solution was composed per liter of 125 g of sodium citrate, 250 g of KH$_2$PO$_4$, 10 g of MgSO$_4$.7H$_2$O, 5 g of CaCl$_2$.2H$_2$O, 2.5 ml of biotin stock solution, and 5 ml of 200×AMG Trace Elements Solution.

Biotin stock solution was composed of 5 mg of biotin in 100 ml of 50% ethanol.

200×AMG Trace Metals was composed per liter of 3 g of citric acid, 14.3 g of ZnSO$_4$.7H$_2$O, 2.5 g of CuSO$_4$.5H$_2$O, 13.8 g of FeSO$_4$.7H$_2$O, and 8.5 g of MnSO$_4$.H$_2$O.

Vogel's Salts medium was composed per liter of 20 ml of filter sterilized (0.2 μm diameter pore size, Fisher Millipore) 50× Vogel's salts solution, 16.5 g of monobasic ammonium phosphate, and 50 g of sucrose, pH buffered to 6.50 using 5N NaOH prior to autoclaving for 25 minutes. Prior to inoculation, when the solution had cooled, 2.5 ml BASTA were added from a filter sterilized 250 mg/ml stock solution for a final concentration of 6 mg/ml.

SY50 medium was composed per liter of 50 g of sucrose, 2 g of MgSO$_4$.7H$_2$O, 10 g of KH$_2$PO$_4$, 2 g of K$_2$SO$_4$, 2 g of citric acid H$_2$O, 10 g of yeast extract, 2 g of urea, 0.5 g of CaCl$_2$.2H$_2$O, and 0.5 ml of 200×AMG trace metals solution; adjusted pH to 6.00 with 5 N NaOH prior to autoclaving for 25 minutes.

STC was composed of 0.8 M sorbitol, 50 mM CaCl$_2$, and 25 mM Tris-Cl, pH 8.

SPTC was composed of 0.8 M sorbitol, 25 mM Tris-HCl, pH 8, 50 mM CaCl$_2$, and 40% PEG 4000.

TBE buffer was composed of 50 mM Tris Base, 50 mM boric acid, and 1 mM disodium EDTA.

Example 1

Production of *Fusarium venenatum* Mycelial Tissue

*Fusarium venenatum* CC$_{1-3}$, a morphological mutant of *Fusarium* strain (NRRL 30747 or ATCC 20334) (Wiebe et al., 1991, *Mycological Research* 95: 1284-1288), was grown in a two-liter lab-scale fermentor using a fed-batch fermentation scheme with NUTRIOSE™ (Roquette Freres, S. A., Beinheim, France) as the carbon source and yeast extract. Ammonium phosphate was provided in the feed. The pH was maintained at 6 to 6.5, and the temperature was kept at 30° C. with positive dissolved oxygen.

Mycelial samples were harvested at 4 days post-inoculum and quick-frozen in liquid nitrogen. The samples were stored at −80° C. until they were disrupted for RNA extraction.

Example 2 cDNA Library Construction

Total cellular RNA was extracted from the mycelial samples described in Example 1 according to the method of Timberlake and Barnard (1981, *Cell* 26: 29-37), and the RNA samples were analyzed by Northern hybridization after blotting from 1% formaldehyde-agarose gels (Davis et al., 1986, *Basic Methods in Molecular Biology*, Elsevier Science Publishing Co., Inc., New York). Polyadenylated mRNA fractions were isolated from total RNA with an mRNA Separator Kit™ (Clontech Laboratories, Inc., Palo Alto, Calif.) according to the manufacturer's instructions. Double-stranded cDNA was synthesized using approximately 5 µg of poly(A)+ mRNA according to the method of Gubler and Hoffman (1983, *Gene* 25: 263-269) except a Not I-(dT)18 primer (Pharmacia Biotech, Inc., Piscataway, N.J.) was used to initiate first strand synthesis. The cDNA was treated with mung bean nuclease (Boehringer Mannheim Corporation, Indianapolis, Ind.) and the ends were made blunt with T4 DNA polymerase (New England Biolabs, Beverly, Mass.).

The cDNA was digested with Not I, size selected by agarose gel electrophoresis (ca. 0.7-4.5 kb), and ligated with pZErO-2.1 (Invitrogen, Carlsbad, Calif.) which had been cleaved with Not I plus Eco RV and dephosphorylated with calf-intestine alkaline phosphatase (Boehringer Mannheim Corporation, Indianapolis, Ind.). The ligation mixture was used to transform competent *E. coli* TOP10 cells (Invitrogen, Carlsbad, Calif.). Transformants were selected on 2YT agar plates (Miller, 1992, *A Short Course in Bacterial Genetics. A Laboratory Manual and Handbook for Escherichia coli and Related Bacteria*, Cold Spring Harbor Press, Cold Spring Harbor, N.Y.) which contained kanamycin at a final concentration of 50 µg/ml.

A directional cDNA library was constructed using the plasmid cloning vector pZErO-2.1. Library D was made using mRNA from mycelia harvested at four days and cDNA library was amplified. The library was plated, titered, and independent clones were analyzed by DNA sequencing.

Library D consisted of about $7.5 \times 10^4$ independent clones before amplication. Miniprep DNA was isolated from forty colonies in each library and checked for the presence and size of cDNA inserts. In this analysis 39 of 40 colonies (97.5%) from Library D contained inserts with sizes ranging from 600 by to 2200 by (avg.=1050 bp)

Example 3

Template Preparation and Nucleotide Sequencing

From the cDNA library described in Example 2, 1152 transformant colonies were picked directly from the transformation plates into 96-well microtiter dishes which contained 200 µl of 2YT broth (Miller, 1992, supra) with 50 µg/ml kanamycin. The plates were incubated overnight at 37° C. without shaking. After incubation 100 µl of sterile 50% glycerol were added to each well. The transformants were replicated into secondary, deep-dish 96-well microculture plates (Advanced Genetic Technologies Corporation, Gaithersburg, Md.) containing 1 ml of Magnificent Broth™ (MacConnell Research, San Diego, Calif.) supplemented with 50 µg of kanamycin per ml in each well. The primary microtiter plates were stored frozen at −80° C. The secondary deep-dish plates were incubated at 37° C. overnight with vigorous agitation (300 rpm) on rotary shaker. To prevent spilling and cross-contamination, and to allow sufficient aeration, each secondary culture plate was covered with a polypropylene pad (Advanced Genetic Technologies Corporation, Gaithersburg, Md.) and a plastic microtiter dish cover.

DNA was isolated from each well using the 96-well Miniprep Kit protocol of Advanced Genetic Technologies Corporation (Gaithersburg, Md.) as modified by Utterback et al. (1995, *Genome Sci. Technol.* 1:1-8). Single-pass DNA sequencing was done with a Perkin-Elmer Applied Biosystems Model 377 XL Automatic DNA Sequencer (Perkin-Elmer Applied Biosystems, Inc., Foster City, Calif.) using dye-terminator chemistry (Giesecke et al., 1992, *Journal of Virology Methods* 38: 47-60) and the reverse lac sequencing primer.

Example 4

Analysis of DNA Sequence Data

Nucleotide sequence data were scrutinized for quality, and samples giving improper spacing less than or equal to 9.2 or ambiguity levels exceeding 3% were discarded or re-run. Vector sequences were trimmed with assistance of FACTURA™ software (Perkin-Elmer Applied Biosystems, Inc., Foster City, Calif.). In addition, sequences were truncated at the end of each sample when the number of ambiguous base calls increased. All sequences were compared to each other to construct overlapping contigs using TIGR Assembler software (Sutton, G. G. et al., 1995, *Genome Science and Technology* 1: 9019) to determine multiplicity of various cDNA species represented in each library. Lastly, all sequences were translated in three frames and searched against a non-redundant data base (NRDB) using GeneAssist™ software (Perkin-Elmer Applied Biosystems, Inc., Foster City, Calif.) with a modified Smith-Waterman algorithm using the BLOSUM 62 matrix with a threshold score of 70. The NRDB was assembled from Genpept, Swiss-Prot, and PIR databases.

Example 5

Identification of Alpha-Glucosidase cDNA Clones

Putative alpha-glucosidase clones were identified by partial sequencing of random cDNA clones using an Applied Biosystems Model 377 XL Automated DNA Sequencer according to the manufacturer's instructions and comparison of the deduced amino acid sequence to the sequences in the NRDB as described in Example 4. From the 1152 cDNA sequences analyzed, eleven clones from Library D showed amino acid sequence homology to alpha-glucosidase proteins from other fungi and yeasts. Among several alpha-glucosidase cDNA clones discovered in this manner, two were estimated to be full-length (encoding the complete protein) on the basis of its alignment to the *Neurospora crassa* (SWALL accession number Q872B7) and *Aspergillus nidulans* (SWALL accession number Q9C1S7) alpha-glucosidase amino acid sequences and the presence of a possible signal peptide, detected using the Signal-P computer program (Nielsen, et al., 1997, *Protein Engineering* 10:1-6). The clone designated *E. coli* FD11F2 containing plasmid pFD11F2 was selected for expression in *Fusarium venenatum* (see Example 7). *E. coli* FD11F2 containing plasmid pFD11F2 was deposited with the Agricultural Research Service Patent Culture Collection, Northern Regional Research Center, 1815 University Street, Peoria, Ill., 61604, as NRRL B-30753, with a deposit date of Jul. 1, 2004.

Example 6

Isolation, Nucleotide Sequencing and Characterization of a cDNA Segment Encoding Fusarium venenatum Alpha-Glucosidase DNA sequencing of the cloned insert in pFD11F2 was done with an Applied Biosystems Model 3700 Automated DNA Sequencer using dye-terminator chemistry. Contiguous sequences were generated using a primer walking strategy and assemblied using phred/phrap/consed (University of Washington). The inserted sequence in pFD11F2 was sequenced to an average error rate of less than 1 base per 10,000 bases.

By comparing the cDNA sequence data to the contig of alpha-glucosidase cDNA sequences, it was determined that the cDNA segment encoding *Fusarium venenatum* alpha-glucosidase contained an open reading frame of 2880 by encoding a polypeptide of 960 amino acids. The nucleotide sequence (SEQ ID NO: 1) and deduced amino acid sequence (SEQ ID NO: 2) are shown FIGS. 1A and 1B. The G+C content of SEQ ID NO: 1 is 52.3% and of nucleotides 61 to 2880 of SEQ ID NO: 1 is 52.1%. Using the SignalP version 2.0 program (Nielsen et al., 1997*, Protein Engineering* 10:1-6), a signal peptide of 20 residues was predicted. The predicted mature protein contains 960 amino acids with a molecular mass of 105.8 kDa.

A comparative alignment of fungal alpha-glucosidase protein sequences was undertaken using the Clustal method (Higgins, 1989*, CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the *Fusarium venenatum* alpha-glucosidase shares identity with the following alpha-glucosidases from other fungi (percent identical residues in parentheses): *Aspergillus nidulans* accession number Q9C1 S7 (77%), *Neurospora crassa* accession number Q872B7 (53%), *Acremonium implicatum* accession number BAD08418 (51%), *Mucor javanicus* accession number Q92442 (37%), and *Aspergillus niger* accession number P56526 (31%).

Example 7

Construction of pEJG61

The *Fusarium venenatum* expression vector pEJG61 was generated by modification of pSheB1 (U.S. Pat. No. 6,090,604). The modifications included (a) changing the single Bsp LU11I site in pSheB1 by site-directed mutagenesis (b) replacement of 930 by of the *Fusarium oxysporum* trypsin promoter with 2.1 kilobases of the *Fusarium venenatum* glucoamylase promoter, and (c) introduction of a Bsp LU11I site after the *Fusarium venenatum* glucoamylase promoter.

Removal of the Bsp LU11I site within the pSheB1 sequence was accomplished using the QuikChange™ Site-Directed Mutagenesis Kit (Stratagene Cloning Systems, La Jolla, Calif.) according to the manufacturer's instruction with the following pairs of mutagenesis primers:

```
5'-GCAGGAAAGAACAAGTGAGCAAAAGGC-3'    (SEQ ID NO: 3)

5'-GCCTTTTGCTCACTTGTTCTTTCCTGC-3'    (SEQ ID NO: 4)
```

This created pSheB1 intermediate 1.

Removal of 930 by of the *Fusarium oxysporum* trypsin promoter was accomplished by digesting pSheB1 intermediate 1 (6,971 bp) with Stu I and Pac I, subjecting the digest to electrophoresis on a 1% agarose gel, at 100 volts for one hour using TBE buffer, excising the 6,040 by vector fragment, and purifying the excised fragment with a Qiaquick Gel Purification Kit (QIAGEN Inc., Valencia, Calif.). To introduce a new Bsp LU11I site, a linker was created using the following primers:

```
5'-dCCTACATGTTTAAT-3'        (SEQ ID NO: 5)
     Bsp Lu11I
5'-dTAAACATGTAGG-3'          (SEQ ID NO: 6)
```

Each primer (2 μg each) was heated to 70° C. for 10 minutes and then cooled to room temperature over an hour. This linker was ligated into the Stu I-Pac I digested pSheB1 intermediate 1 vector fragment, creating pSheBI intermediate 2.

A 2.1 kilobase fragment of *Fusarium venenatum* genomic DNA 5 prime of the glucoamylase coding region (glucoamylase promotor) was isolated by PCR of plasmid pFAMG (WO 00/56900) containing *Fusarium venenatum* genomic DNA encoding the entire coding region for *Fusarium venenatum* glucoamylase and 3,950 by of upstream sequence. The primers used for PCR follow:

```
5'-AGGCCTCACCCATCTCAACAC-3'    (SEQ ID NO: 7)

5'-ACATGTTGGTGATAGCAGTGA-3'    (SEQ ID NO: 8)
```

The PCR reaction (50 μl) was composed of 200 ng of pFAMG, 200 μM dNTPs, 1 μM of the above primers, 1× reaction buffer, and 2.6 units of Expand High Fidelity enzyme mix. The reactions were incubated using a MJ Research Thermocycler (MJ Research, Inc., Boston, Mass.) programmed for 1 cycle 1 at 94° C. for 2 minutes; 10 cycles each at 94° C. for 15 seconds, 60° C. for 30 seconds, and 72° C. for 2 minutes and 15 seconds; 15 cycles each at ° G4 for 15 seconds, 60° C. for 30 seconds, and 72° C. for 2 minutes and 15 seconds with 5 seconds cycle elongation for each successive cycle; and 1 cycle at 72° C. for 7 minutes.

The PCR product was subjected to electrophoresis on a 1% agarose gel at 100 volts for one hour using TBE buffer generating an expected band of 2,108 bp. The 2,108 by PCR product was excised from the agarose gel and purified with a Qiaquick Gel Purification Kit (QIAGEN Inc., Valencia, Calif.). This fragment was cut with Stu I and Bsp LU11I, purified with a Qiaquick Purification Kit (QIAGEN Inc., Valencia, Calif.), and ligated into Stu I-Bsp LU11I digested pSheBI intermediate 2 creating pEJG61 (FIG. 2).

Example 8

Construction of *Fusarium venenatum* Alpha-Glucosidase Expression Vectors

An InFusion Cloning Kit (BD Biosciences, Palo Alto, Calif.) was used to clone the PCR fragment containing the alpha-glucosidase gene directly into the expression vector, pEJG61, without the need for restriction digests and ligation. The cDNA clone was subjected to PCR amplification using gene-specific forward and reverse primers shown below. Bold letters represent coding sequence while underlined letters represent added Bsp LU11I and Pac I sites to the 5' and 3' ends of the alpha-glucosidase gene, respectively. The remaining sequence is homologous to the insertion sites of pEJG61.

Primer 997154 (5' BspLU11I Fv a-GS): (SEQ ID NO: 9)

5'-CACTGCTATCACCAACATGTTCTTCAAGAAGCTGCT-3'

Primer 997155 (3' PacI Fv a-GS): (SEQ ID NO: 10)

5'-CCAACAAGGTATTTAATTAATCAGAAGAGATCCAC-3'

The PCR amplification was performed using an Expand High Fidelity PCR System (Roche, Indianapolis, Ind.)

according to manufacturer's instructions. Each PCR reaction (50 µl) was composed of 200 ng of cDNA clone template, 200 µM dNTPs, 1 µM forward and reverse primers, 1× reaction buffer, and 2.6 units of Expand High Fidelity enzyme mix. The reactions were incubated using a MJ Research Thermocycler programmed for 1 cycle 1 at 94° C. for 2 minutes; 10 cycles each at 94° C. for 15 seconds, 60° C. for 30 sec, and 72° C. for 1 minute and 15 seconds; 15 cycles each at 94° C. for 15 seconds, 60° C. for 30 seconds, and 72° C. for 1 minutes and 15 seconds with 5 seconds cycle elongation for each successive cycle; and 1 cycle at 72° C. for 7 minutes. An aliquot of each PCR product was run on a 0.7% agarose gel using TBE buffer generating expected bands of approximately 3 bp.

Figure 3:
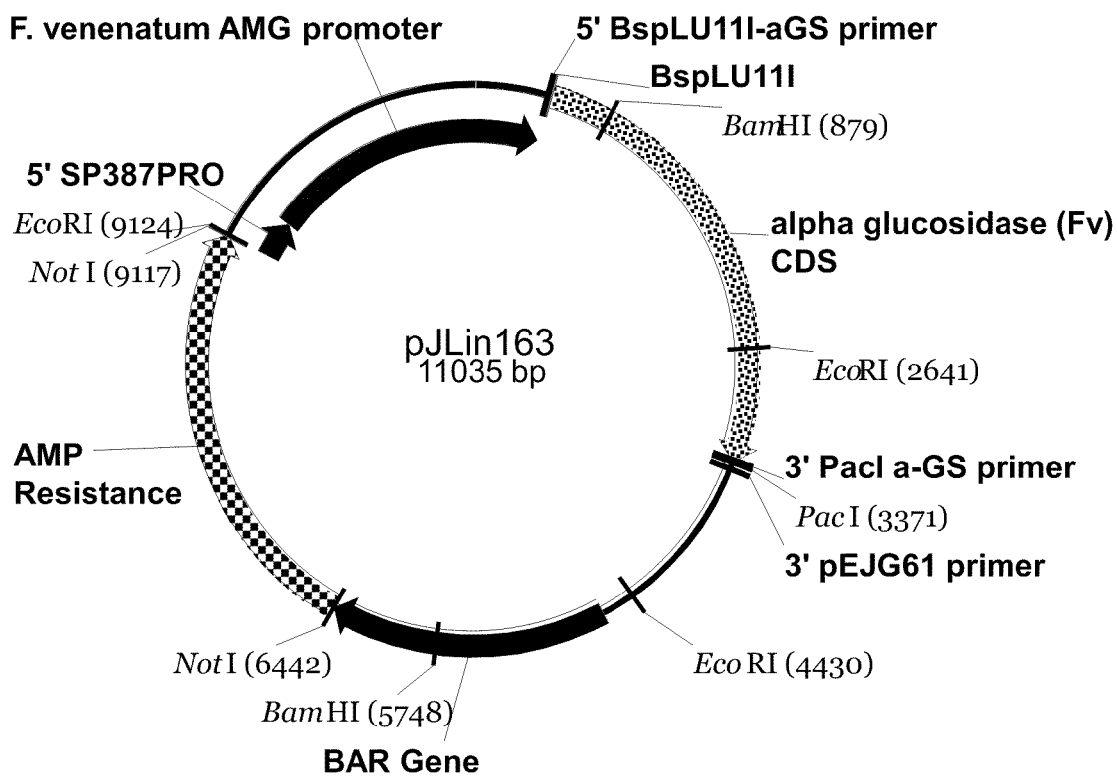
FIG. 3 shows a restriction map of pJLin163.

The PCR product was gel purified using a QIAquick Gel Extraction Kit (Qiagen Inc., Valencia, Calif.), and then cloned into the pEJG61 expression vector using an InFusion Cloning Kit (BD Biosciences, Palo Alto, Calif.), resulting in plasmid pJLin163 (FIG. 3). The InFusion Cloning reaction (50 µl) was composed of 1× InFusion Buffer (BD Biosciences, Palo Alto, Calif.), 1× BSA (BD Biosciences, Palo Alto, Calif.), 1 µl of Infusion enzyme (diluted 1:10), 100 ng of pEJG61 digested with Bsp LU11I and Pac I, and 50 ng of the purified PCR product containing the alpha-glucosidase gene. The reaction was incubated at room temperature for 30 minutes.

Two µls of the reaction was used to transform *E. coli* Solopac Gold supercompetent cells (Stratagene, La Jolla, Calif.) according to the manufacturer's instructions. An *E. coli* transformant containing the pJLin163 plasmid was isolated and confirmed by sequence analysis using an Applied Biosystems Model 377 Sequencer XL using dye-terminator chemistry.

Example 9

Transformation of pJLin163 into *Fusarium venenatum* WTY842-1-11

Spores of *Fusarium venenatum* strain WTY842-1-11 (Δtrichodiene synthase, amdS+) a mutant of *Fusarium* strain A3/5 (NRRL 30747 or ATCC 20334) (Wiebe et al., 1992, *Mycological Research* 96: 555-562; Wiebe et al., 1991, *Mycological Research* 95: 1284-1288; Wiebe et al., 1991, *Mycological Research* 96: 555-562), were generated by inoculating a flask containing 100 ml of RA sporulation medium with 8 plugs from an agar plate and incubated at 27° C., 150 rpm for 24 hours, then 24 hours, 150 rpm at 22° C. Spores were harvested by filtering culture through Miracloth onto a Nalgene 0.2 µm filter. Wash spores twice with sterile distilled water, resuspended in a small volume of water, and then counted using a hemocytometer.

Protoplasts were prepared by inoculating 100 ml of YPG medium with $2 \times 10^8$ spores of *Fusarium venenatum* WTY842-1-11 and incubating for 15 hours at 18° C. and 150 rpm. The culture was filtered through Miracloth, washed once with sterile distilled water and once with 1 M $MgSO_4$ and resuspended in 40 ml of 5 mg/ml of NOVOZYME 234™ in 1 M $MgSO_4$. Cultures were incubated at 29° C. and 90 rpm until protoplasts formed. A volume of 30 ml of 1 M sorbitol was added to the protoplast digest and the mixture was centrifuged at 1500 rpm for 10 minutes. The pellet was resuspended, washed twice with 1 M sorbitol, and centrifuged at 1500 rpm for 10 minutes to pellet the protoplasts. Protoplasts were counted with a hemocytometer and resuspended in an 8:2:0.1 solution of STC:SPTC:DMSO to a final concentration of $5 \times 10^7$ protoplasts/ml. The protoplasts were stored at –80° C., after controlled-rate freezing in a Nalgene Cryo 1° C. Freezing Container.

Two ml of protoplast suspension were added to 100 µg of pJLin163 circular plasmid and 250 µg heparin in a 50 ml Falcon tube, mixed and incubated on ice for 30 minutes. Two hundred µl of SPTC was mixed gently into the protoplast suspension and incubation was continued at room temperature for 10 minutes. Twenty ml of SPTC was mixed gently into the protoplast suspension and incubation was continued at room temperature for 10 minutes. A 350 ml volume of molten Vogel's $NO_3$ Regeneration Low-Melt medium (cooled to 50° C.) was mixed with the protoplasts and then 35 ml were plated onto 100 mm Petri plate containing 35 ml of the identical medium plus 12 mg of BASTA™ per ml. Incubation was continued at room temperature for 10 to 14 days. After 12 days, 21 transformants were apparent. A mycelial fragment from the edge of each transformant was transferred to plates containing Vogel's $NO_3$ Regeneration Low-Melt medium+BASTA (6 mg/ml) medium. The plate was sealed in a plastic bag to maintain moisture and incubated approximately one week at room temperature.

The transformants of *Fusarium venenatum* WTY842-1-11 were grown in 25 ml of M400 medium in a 125 ml shake flask. The cultures were incubated at 28° C. and 200 rpm. On days 2, 4, and 6, culture supernatants were harvested and assayed for alpha-glucosidase activity. Culture supernatants were diluted in 0.1 M sodium acetate buffer pH 4.3 in series from 0-fold to ⅓-fold to ⅑-fold. An AMG standard obtained from Novozymes A/S, Bagsværd, Denmark, was diluted using 2-fold steps starting with a 0.033 AGU/ml concentration and ending with a 0.0042 AGU/ml concentration in 0.1 M sodium acetate buffer pH 4.3. A total of 100 µl of each dilution including standard was transferred to a 96-well flat bottom plate. Fifty micro-liters of a 20 mg/ml maltose solution was added to each well then incubated at 25° C. for 180 minutes. Upon completion of the incubation step 100 µl of a 0.06 N NaOH solution was added to each well to quench the reaction. A total of 30 µl was transferred from each well and placed into a new 96-well plate followed by the addition of 200 µl of liquid glucose (oxidase) reagent (Pointe Scientific, Inc, Lincoln Park, Mich., USA) to each well and incubated at ambient temperature for 8 minutes. Upon completion of the incubation, the absorbance at 490 nm was measured for the 96-well plate using a Spectra Max 349 (Molecular Devices, Sunnyvale, Calif.). Sample concentrations were determined by extrapolation from the generated standard curve. The glucose content present in the medium was normalized by independently measuring glucose in the sample broth by the Liquid Glucose Reagent without addition of maltose. The absorbance was subtracted from the value from reagents in which maltose substrate was added.

All of the twenty transformants expressed alpha-glucosidase. The highest producing transformant was transformant 13.1.G24. Expression peaked on day 6 (FIG.). Untransformed strain *Fusarium venenatum* WTY842-1-11 had no detectable activity. Transformant 13.1.G24 strain was renamed as *Fusarium venenatum* JLin725.

Example 10

Fermentation of *Fusarium venenatum* JLin725

*Fusarium venenatum* JLin725 was evaluated for its ability to produce alpha-glucosidase by fermentation.

All fermentations were started in a 2-stage liquid seed. The first stage was in 100 ml of Vogel's Salts medium in a 500 ml unbaffled plastic shake flask, capped with silicone sponge closures. The medium was composed per liter of 20 ml of filter sterilized (0.2 μm diameter pore size, Fisher Millipore) Vogel's salts stock solution (prepared at 50× final concentration), 16.5 g of monobasic ammonium phosphate, and 50 g of sucrose, pH buffered to 6.50 using 5N NaOH prior to autoclaving for 25 minutes. Prior to inoculation, when the solution had cooled, 2.5 ml of BASTA were added from a filter sterilized 250 mg/ml stock solution for a final concentration of 6 mg/ml.

Shake flasks were then inoculated with an approximately 1 cm$^2$ plug cut from a fresh seven-day old agar culture plate. The flasks were then incubated for approximately 72 hours at 200 rpm and 28° C.

Second stage seeds were also prepared in 500 ml shake flasks with silicone sponge closures, using 100 ml of SY50 medium. Second stage seeds were inoculated with 0.3 ml of culture from the first stage seed. These seeds were then incubated at 28° C., 200 rpm for approximately 48 hours.

Fed-batch fermentors were set up in Applikon 3L jacketed glass bioreactors. The medium, made in tap water, was composed per liter of 20 g of sucrose, 2 g of MgSO$_4$.7H$_2$O, 2 g of KH$_2$PO$_4$, 2 g of citric acid, 5.6 g of (NH$_4$)$_2$HPO$_4$, 0.5 ml of 200×AMG Trace Metals, 0.5 g of CaCl$_2$.2H$_2$O, and 30 ml of a vitamin stock solution (0.15 g of thiamine HCl, 0.08 g of riboflavin, 0.4 g nicotinic acid, 0.5 g calcium pantothenate, 0.005 g of biotin, 0.05 g of folic acid, 0.1 g of pyridoxal-HCl, in deionized water, mixed over heat and filtered through a 0.45 μm filter (Millipore, Bedford, Mass.)). This batch mixture was adjusted to pH 6.50 with 5 N NaOH.

A total of 20 g of soy concentrate was added separately to each tank prior to filling with 1800 ml of medium. The headplate was then loosely installed and moderate agitation commenced to thoroughly mix and wet the soy powder. Approximately 0.9 ml of pluronic acid was also added at this time to minimize foaming.

The feed was made up in 2 liter plastic bottles, consisting of 495 g of maltose and tap water to make the final mass 1500 g. Pluronic acid (1 ml) was added prior to mixing.

The pH was controlled at 6.25+/−0.25 using 15% NH$_4$OH solution in a tightly capped bottle, and 5 NH$_3$PO$_4$. Tanks were operated at 1200 rpm agitation and 1 vvm airflow, with temperature at 29° C.+/−1° C. Inoculation from the second stage seeds was with 50 ml of culture aseptically transferred to a 60 ml syringe which was injected into the tank.

Feed was started after approximately 19 hours, after pH has dropped to the bottom of the control band and then risen again to the top of the control band, signifying depletion of batch nutrients. Feed is at a constant 3.78 g/L-hr for the length of the fermentation. DO concentration was maintained above 30%.

Example 11

Purification and Characterization of *Fusarium venenatum* Alpha-Glucosidase

Alpha-glucosidase activity was measured using maltose as substrate. Samples of 25 μl were mixed with 375 μl of a 1.1% maltose solution in 50 mM acetate buffer, pH 5.0. The mixture was incubated for 10 minutes at 37° C. Then 100 μl of 1 M Tris was added and a portion of the resulting solution was transferred to an Eppendorf tube and placed into boiling water for 3-4 minutes to quench the enzymatic hydrolysis of maltose. To measure the liberated glucose, a 20 μl aliquot was transferred to a well of 96-well microplate and mixed with 200 μl of glucose oxidase-horseradish peroxidase-2,2'-azino-bis(3-ethylbenz-thiazoline-6-sulfonic acid) diammonium salt solution (0.6 g/l glucose oxidase, 0.02 g/l horseradish peroxidase and 1.0 g/l 2,2'-azino-bis(3-ethylbenz-thiazoline-6-sulfonic acid) diammonium salt in 100 mM sodium phosphate pH 7.0). After incubation for 30 minutes at room temperature, the absorbance at 420 nm was measured using a Spectra Max 349 (Molecular Devices, Sunnyvale, Calif.).

Protein concentration was measured using a BCA Protein Assay Reagent (Pierce, Rockford, Ill.) according to the manufacturer's instructions.

*Fusarium venenatum* alpha-glucosidase was purified from a fermentation broth supernatant produced by cultivation of *Fusarium venenatum* strain WTY842-1-11 (Δtri5, amdS$^+$) as described in Example 10.

The culture broth supernatant (approximately 0.45 liter) was prepared by centrifugation of the whole fermentation broth, and then filtered using Nalgene Filterware equipped with a 0.22 mm filter, diluted with 100 mM Tris-HCl pH 8.0 buffer, and concentrated using an Amicon Spiral Ultrafiltration System equipped with a PM 10 ultrafiltration membrane. The final preparation had a pH of 8.0 and conductivity of 7.2 mS It was loaded onto a 24×390 mm column containing approximately 200 ml of Q-Sepharose, Big Beads (Pharmacia Biotech AB, Uppsala, Sweden) pre-equilibrated with 100 mM Tris-HCl pH 8.0 buffer. Protein with alpha-glucosidase activity was eluted with a 700 ml gradient from 0 to 0.8 M NaCl in 50 100 mM Tris-HCl pH 8.0 buffer. Fractions with alpha-glucosidase activity were pooled, desalted using a PM 10 membrane, and equilibrated with 100 mM Tris-HCl pH 8.0 buffer.

The pooled solution was then loaded onto a 20 ml Pharmacia MonoQ Beads column pre-equilibrated with 100 mM Tris-HCl pH 8.0 buffer. Fractions with alpha-glucosidase activity were pooled, concentrated and equilibrated with 100 mM Tris-HCl pH 8.0 buffer, 1.7M (NH$_4$)$_2$SO$_4$.

Finally, the concentrated sample was loaded onto a Pharmacia Phenyl Superose 5/5 pre-packed 7×50 mm column (Pharmacia Biotech AB, Uppsala, Sweden) pre-equilibrated with 100 mM Tris-HCl pH 8.0 buffer, containing 1.7M (NH$_4$)$_2$SO$_4$. Protein with alpha-glucosidase activity was then eluted with a 300 ml gradient from 1.7 to 0 M (NH$_4$)$_2$SO$_4$ in 100 mM Tris-HCl pH 8.0 buffer. Fractions containing alpha-glucosidase activity were analyzed by standard SDS-PAGE and native gel and then pooled.

Table 1 summarizes the purification of alpha-glucosidase.

TABLE 1

Summary of Purification of Alpha-Glucosidase

| | Volume (ml) | Protein (mg) | % Total activity[1] |
|---|---|---|---|
| Initial supernatant | 775 | 891 | 100 |
| Acetate wash on Q-Sepharose (pigment removal) | 250 | 95 | 82.3 |
| Q-Sepharose column chromatography | 264 | 32 | 82.3 |
| MonoQ column chromatography | 90 | 15 | 51.9 |
| Phenyl Superose column chromatography | 21 | 9 | 41.0 |

[1]Alpha-glucosidase activity was measured at pH 5.0 using maltose as a substrate (AMG activity-assay protocol. Maltose solution was preheated up to 37° C. The incubation with the enzyme was done at room temperature).

A native gel (BioRad Precast Polyacrylamide Gel, Bio-Rad Laboratories, Inc., Hercules, Calif.) was run to determine whether the alpha-amylase was composed of several sub-units. The sample buffer was 4.0 ml of 0.5 M Tris-HCl pH 8.8, 0.5 ml of 0.1% bromophenol blue, 2.0 ml of glycerol, and distilled water to 10.0 ml. The running buffer was composed per liter of 2.9 g of Tris Base and 14.4 g of glycine, adjusted to pH 8.3. The gel was run at 200 V for 1 hour and stained as described in Example 9. The native gel showed only one band with a molecular weight around 140 kDa, suggesting the enzyme was not composed of subunits.

pH optmum. Specific activity of the purified *Fusarium venenatum* alpha-glucosidase was measured at different pH values in 50 mM acetate buffer/50 mM phosphate buffer at 37° C. using the activity assay described above.

Figure 4:
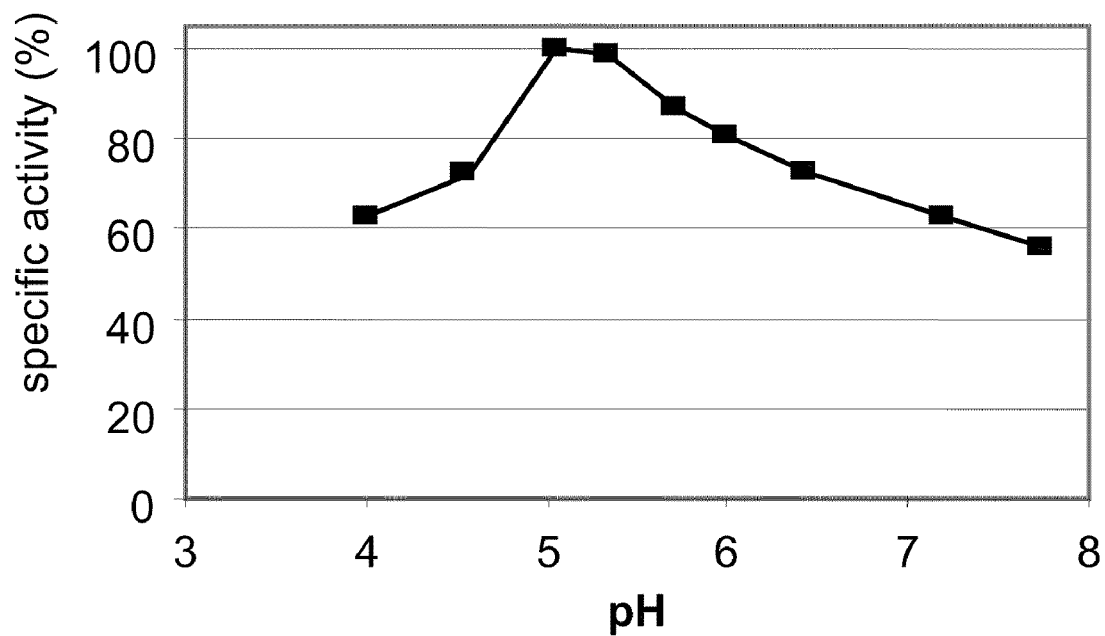
FIG. 4 shows the dependence of the purified *Fusarium venenatum* alpha-glucosidase on pH in 50 mM sodium acetate-50 mM potassium phosphate at 37° C.

*Fusarium venenatum* alpha-glucosidase has pH optimum of activity as shown in FIG. 4 in the range of about 4.5 to about 6.0, preferably about 4.7 to about 5.7, more preferably about 4.8 to about 5.5, most preferably about 5.0 to about 5.3, and even most preferably at pH 5.0.

Thermostability. The thermostability of the purified *Fusarium venenatum* alpha-glucosidase was determined by incubating the alpha-glucosidase in 50 mM sodium acetate pH 5.0 for 5 minutes in a water bath at the following temperatures: 35, 45, 50, 55, 60, 65, 71 and 100. Maltose as a substrate (1.1%; 375 µl) was incubated for 5 minutes in a water bath at 37° C. An aliquot of the enzyme sample was mixed with the substrate and specific activity was measured at 37° C.

Figure 5:
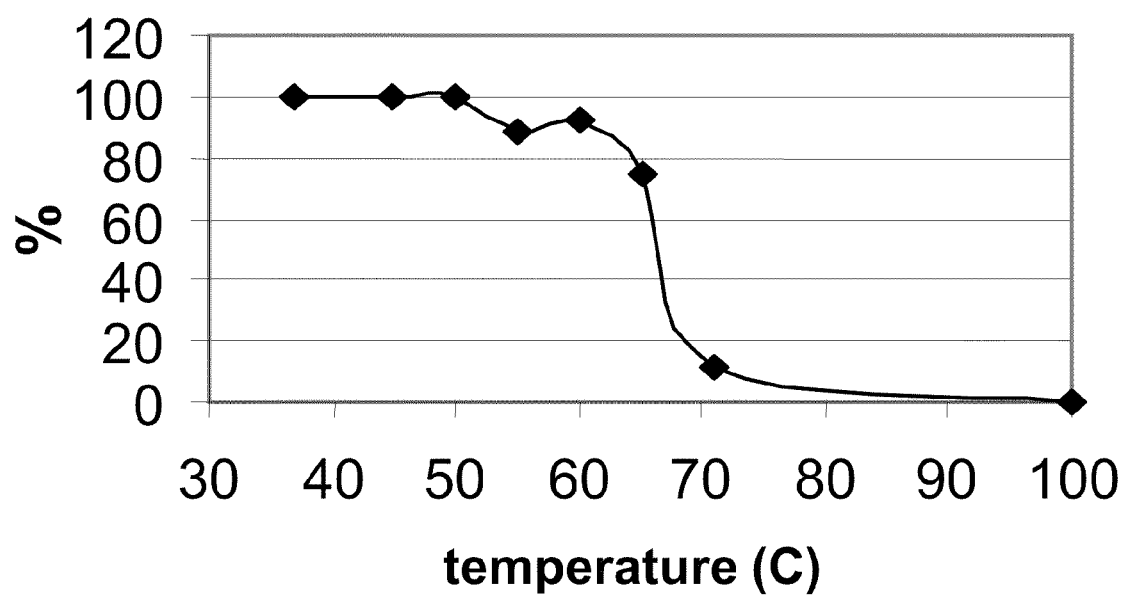
FIG. 5 shows the thermostability of the purified *Fusarium venenatum* alpha-glucosidase after incubation in 50 mM sodium acetate pH 5.0 for 5 minutes at different temperatures.

The *Fusarium venenatum* alpha-glucosidase has good thermostability (approximately 77% residual) up to about 65° C. as shown in FIG. 5. The enzyme loses only 23% activity after 5 minutes in 50 mM acetate buffer pH 5.0 at this temperature and loses all activity at 100° C.

Kinetic parameters. The kinetic parameters for the specific hydrolysis of maltose by the purified *Fusarium venenatum* alpha-glucosidase were determined.

A Dionex BioLC HPLC device equipped with CarboPac PA10 4×250 mm column and ED50 Electrochemical detector (Sunnyvale, Calif.) was used to detect glucose quantitatively from the hydrolysis of maltose. Sodium hydroxide solution (200 mM) was applied as a liquid phase. This method provides precise determination at the level of around 0.01 mM glucose. The calibration curve was linear between 0 mM and 1.2 mM glucose.

The incubation mixture contained 10 ml of maltose solution in the range of 0.17-5.7 mM at 37° C. The enzymatic reaction was initiated by adding 10 µl of alpha-glucosidase solution. The enzymatic reaction was terminated by placing 1 ml aliquot into boiling water for 2.5 minutes and then into ice for at least 30 minutes.

Values of $k_{cat}$ were calculated using a molecular mass of 105.8 kDa.

The reciprocal plots, commonly used for determining kinetic parameters, were not linear for the enzyme. At elevated maltose concentrations, the velocity of the hydrolysis reaction (accumulation of glucose) was significantly decreased.

The observed decreased velocity in alpha-glucosidase-catalyzed hydrolysis of maltose may be caused by substrate inhibition (Segel, I. H. Enzyme Kinetics. Behavior and Analysis of Rapid Equilibrium and Steady-State Enzyme Systems. 1975, John Wiley & Sons), or may alternatively be the result of a competitive utilization of glucose in a transglycosylation reaction. As concentrations of maltose are increased, it becomes an acceptor for the glucose molecule. The transglycosylation reaction between the glucose and maltose leads to panose (6-O-alpha-D-glucosylmaltose). The probability of interaction between two glucose molecules, which results in maltose and isomaltose, was low due to the low concentration of maltose at the "initial rate" regime. The CarboPac PA10 column allows separation of glucose from oligosaccharides, but does not separate maltose and panose.

Kinetic parameters for the *Fusarium venenatum* alpha-glucosidase were estimated from the plots. At pH 5.0 and 37° C., the $K_m$ for the *Fusarium venenatum* alpha-glucosidase was 0.13 mM and $k_{cat}$ was 17 s$^{-1}$ (substrate interval 0.17 mM-1.0 mM).

As indicated above, the substrate intervals were not always optimal. At the same time the detection limit did not allow the application of lower substrate concentrations. The *Fusarium venenatum* alpha-glucosidase demonstrated strong "substrate inhibition" that can likely be attributed to the transglycosylation activity.

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
| --- | --- | --- |
| *E. coli* pFD11F2 | NRRL B-30753 | Jul. 1, 2004 |

The strain has been deposited under conditions that assure that access to the cultures will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strains. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A transgenic plant, plant part or plant cell, which has been transformed with a polynucleotide encoding a polypeptide having alpha-glucosidase activity, wherein the polypeptide is selected from the group consisting of:
   (a) a polypeptide comprising an amino acid sequence having at least 95% sequence identity with amino acids 21 to 960 of SEQ ID NO: 2;
   (b) a polypeptide that is encoded by a polynucleotide that hybridizes under at least high stringency conditions with (i) nucleotides 61 to 2880 of SEQ ID NO: 1, (ii) the genomic DNA sequence comprising nucleotides 61 to 2880 of SEQ ID NO: 1, or (iii) a full-length complementary strand of (i) or (ii); and
   (c) a polypeptide encoded by a polynucleotide comprising a nucleotide sequence having at least 95% sequence identity with nucleotides 61 to 2880 of SEQ ID NO: 1.

2. The transgenic plant, plant part or plant cell of claim 1, which comprises an amino acid sequence having at least 95% sequence identity with amino acids 21 to 960 of SEQ ID NO: 2.

3. The transgenic plant, plant part or plant cell of claim 2, which comprises an amino acid sequence having at least 97% sequence identity with amino acids 21 to 960 of SEQ ID NO: 2.

4. The transgenic plant, plant part or plant cell of claim 1, which is encoded by a polynucleotide that hybridizes under at least high stringency conditions with (i) nucleotides 61 to 2880 of SEQ ID NO: 1, (ii) the genomic DNA sequence comprising nucleotides 61 to 2880 of SEQ ID NO: 1, or (iii) a full-length complementary strand of (i) or (ii).

5. The transgenic plant, plant part or plant cell of claim 4, which is encoded by a polynucleotide that hybridizes under at least very high stringency conditions with (i) nucleotides 61 to 2880 of SEQ ID NO: 1, (ii) the genomic DNA sequence comprising nucleotides 61 to 2880 of SEQ ID NO: 1, or (iii) a full-length complementary strand of (i) or (ii).

6. The transgenic plant, plant part or plant cell of claim 1, which is encoded by a polynucleotide comprising a nucleotide sequence having at least 95% sequence identity with nucleotides 61 to 2880 of SEQ ID NO: 1.

7. The transgenic plant, plant part or plant cell of claim 6, which is encoded by a polynucleotide comprising a nucleotide sequence having at least 97% sequence identity with nucleotides 61 to 2880 of SEQ ID NO: 1.

8. The transgenic plant, plant part or plant cell of claim 1, which comprises the amino acid sequence of SEQ ID NO: 2 or a fragment thereof having alpha-glucosidase activity.

9. The transgenic plant, plant part or plant cell of claim 8, which comprises the amino acid sequence of SEQ ID NO: 2.

10. The transgenic plant, plant part or plant cell of claim 1, which comprises amino acids 21 to 960 of SEQ ID NO: 2.

11. The transgenic plant, plant part or plant cell of claim 1, which consists of SEQ ID NO: 2 or a fragment thereof having alpha-glucosidase activity.

12. The transgenic plant, plant part or plant cell of claim 11, which consists of the amino acid sequence of SEQ ID NO: 2.

13. The transgenic plant, plant part or plant cell of claim 1, which consists of amino acids 21 to 960 of SEQ ID NO: 2.

14. The transgenic plant, plant part or plant cell of claim 1, which is encoded by a polynucleotide comprising the nucleotide sequence of SEQ ID NO: 1 or a subsequence thereof encoding a fragment having alpha-glucosidase activity.

15. The transgenic plant, plant part or plant cell of claim 14, which is encoded by a polynucleotide comprising the nucleotide sequence of SEQ ID NO: 1.

16. The transgenic plant, plant part or plant cell of claim 1, which is encoded by a polynucleotide comprising nucleotides 61 to 2880 of SEQ ID NO: 1.

17. The transgenic plant, plant part or plant cell of claim 1, which is encoded by a polynucleotide consisting of the nucleotide sequence of SEQ ID NO: 1 or a subsequence thereof encoding a fragment having alpha-glucosidase activity.

18. The transgenic plant, plant part or plant cell of claim 1, which is encoded by a polynucleotide consisting of nucleotides 61 to 2880 of SEQ ID NO: 1.

19. The transgenic plant, plant part or plant cell of claim 1, which is encoded by the polynucleotide contained in plasmid pFD11F2 which is contained in *E coli* NRRL B-30753.

20. A method for producing a polypeptide having alpha-glucosidase activity, comprising (a) cultivating the transgenic plant, plant part or plant cell of claim 1 under conditions conducive for production of the polypeptide; and (b) recovering the polypeptide.

* * * * *

SEQUENCE LISTING

<160> NUMBER OF SEQ ID NOS: 10

<210> SEQ ID NO 1
<211> LENGTH: 2883
<212> TYPE: DNA
<213> ORGANISM: Fusarium venenatum

<400> SEQUENCE: 1

```
atgttcttca agaagctgct cacttccgct gcagccctca caggcactgc gcttgcccag      60
agcaaggcag gcgtcgaaga cctcgacaag ccccgcagag acctttttcga aaaggacctc    120
tccaagtgtc ccggctacaa agccacaaag cactgggaga cccgatctgg cttttacgct    180
gacctttccc tcgcgggtca ggcctgtgat gtctacggaa tcgatctgcc tgagctgaaa    240
cttgaggttg aatatcagac cgaagaccga ctgcatgtca agatcttgga tacgaacaac    300
actgtttacc aagtcccaga tgacgttttc cctcgtcctg ggctcggaca gtgggcttca    360
cccaaaaact cgaggctcaa gtttgacttc aaggcggatc ctttctcctt caccgttttcc   420
aggagggata ccgatgaagt gcttttttgat acctcgggca gcgatcttgt ctttgagagt    480
cagtacgtct atctcaagac caagcttccc gatcgccctc atctctacgg tctcggcgag    540
catagcgatc ctttcatgct gaactcgacc aactacaccc gcactatcta cacccgcgac    600
tcatatggta cacccaaggg tcaaaacctc tatggagctc atcccatcta cttcgatcat    660
cgggagaagg gcactcacgg tgttttcctt ctcaactcca acggcatgga cgttttcatc    720
gataagaaga atggccagca gttttttggag tataatatta ttggcggtgt tctcgacttt    780
tacttcgttg ctgggccatc gcctcgtgat gtcgcgaagc agtacgccga gattaccact    840
ctaccccctca tgacgcctta ctggggtctc ggttttcacc agtgccgata cggctaccgt    900
gatgtttatg aggttgctgc tgttgtagcc aactattccg ctgctggaat cccactcgag    960
acgatgtgga cagatattga ctacatggac cgtcgacgca tcttcaccat tgatccagag   1020
cgcttccctg cagacaagta caaggacctt gttgatacga tccatgcacg agaccagaag   1080
tacatcgtca tggttgaccc agccgtatat gacatggaat ctaatccggc ccttgattca   1140
ggcctcgagt acgacacttt catgaaagag cccaacggct ccgactaccg aggtgttgtg   1200
tgggctggac ccagtgtctt ccctgactgg ttcaacccca actcacaaaa gtactggaac   1260
gagctctttg ccaatttctt cgatggcgag aacggtcctg atatcgatgg tctctggatt   1320
gatatgaatg agcctgcaaa cttcttcaac cgtccttacc ctggcaacaa caccactcct   1380
gagaagttcg cagagattga tggtgatccc cccaagccgc ctcccgtccg tgatggtcct   1440
cctgctccta tccctggctt ccccgacagt ctacagcctg catcttctcg tcttaacacg   1500
cgtgagtctg tttccatcgc caagaccacc atccacaagc gctccatggc agcccgcaca   1560
acatcccaca gccgtggcgt tggacagtgg ctaccaaga agcactgggg acagaacaag   1620
tacggccgcc ctggctccag ctggccaaat ggcaagaaga ccggatctgg ttgtggcccg   1680
aatgagtgca agggtcttcc caatcgagag ctcatccagc ctccctacat gatccagaac   1740
ggcgcgggac cgacgcttgc tgacggcact accgataccg atcttgtgca gagcggagat   1800
tacctccagt atgacacaca caacttgtac ggcgctcaga tgtcaacaca ttcgcacaat   1860
gccatgcgtg ctcgacgtcc cgacaagcgc gctcttgtta tcacgcgtag cacctttgct   1920
ggttctggca aggatgtctc gcattggctt ggtgacaacc tctcgatctg ggatcagtac   1980
cgcttttagca ttggtcagct tctccaattt gcatccatct accaaattcc tgttgttggt   2040
```

```
gccgatgtct gtggtttcgg cggtaacgtc actgagactc tatgcgctag atgggctacg   2100
cttggaagtt tctacacttt cttccgtaac cacaacgaga tcactgctgc atcacaagaa   2160
ttctaccgct ggcccaaggt cgccgaggca gcccgtactg gtatcgccat tcgttacaag   2220
ctcctcgatt acatctacac tgccatttac aagcagaacc agacaggcac ccctactctc   2280
aaccctctgt tcttcaacta ccccaacgac aagaacacat actccatcga ccttcagttc   2340
ttttatggtg atggcatcct cgtcagccct gttacaaagg agaacagtac tgagttggaa   2400
tattacctcc ctgatgacat tttctacgag tggtccaccg aaagcctgt tcgtggtact   2460
ggttcatatg agtctgcaga ggttgagctc actgatatca tggttcatta caagggtggc   2520
atcatctacc cccagcgtgt cgacagtgcc aacactacca ccgctctccg caagaagggt   2580
ttcaaccttg ttattgcacc cggtctgaac ggtaaggctt ctggatcttt gtacctcgac   2640
gatggagagt ctgtcgtcca ggacgctgta tccgagattg acttcactta caccaagggc   2700
aagctgagta tgggtggaag cttttgagtac gatgccggtg tcaagattga gacgatcacc   2760
attcttggtg ttgaaaagca gcccaagggc accgatcatg cagagtatga ctctgagaac   2820
aagaagctga tctttgcggc ggatgtacct ttgacgaaga agtgttatgt ggatctcttc   2880
tga                                                                  2883
```

<210> SEQ ID NO 2
<211> LENGTH: 960
<212> TYPE: PRT
<213> ORGANISM: Fusarium venenatum

<400> SEQUENCE: 2

```
Met Phe Phe Lys Lys Leu Leu Thr Ser Ala Ala Leu Thr Gly Thr
1               5                   10                  15

Ala Leu Ala Gln Ser Lys Ala Gly Val Glu Asp Leu Asp Lys Pro Arg
            20                  25                  30

Arg Asp Leu Phe Glu Lys Asp Leu Ser Lys Cys Pro Gly Tyr Lys Ala
        35                  40                  45

Thr Lys His Trp Glu Thr Arg Ser Gly Phe Tyr Ala Asp Leu Ser Leu
    50                  55                  60

Ala Gly Gln Ala Cys Asp Val Tyr Gly Ile Asp Leu Pro Glu Leu Lys
65                  70                  75                  80

Leu Glu Val Glu Tyr Gln Thr Glu Asp Arg Leu His Val Lys Ile Leu
                85                  90                  95

Asp Thr Asn Asn Thr Val Tyr Gln Val Pro Asp Val Phe Pro Arg
            100                 105                 110

Pro Gly Leu Gly Gln Trp Ala Ser Pro Lys Asn Ser Arg Leu Lys Phe
        115                 120                 125

Asp Phe Lys Ala Asp Pro Phe Ser Phe Thr Val Ser Arg Arg Asp Thr
    130                 135                 140

Asp Glu Val Leu Phe Asp Thr Ser Gly Ser Asp Leu Val Phe Glu Ser
145                 150                 155                 160

Gln Tyr Val Tyr Leu Lys Thr Lys Leu Pro Asp Arg Pro His Leu Tyr
                165                 170                 175

Gly Leu Gly Glu His Ser Asp Pro Phe Met Leu Asn Ser Thr Asn Tyr
            180                 185                 190

Thr Arg Thr Ile Tyr Thr Arg Asp Ser Tyr Gly Thr Pro Lys Gly Gln
        195                 200                 205

Asn Leu Tyr Gly Ala His Pro Ile Tyr Phe Asp His Arg Glu Lys Gly
    210                 215                 220
```

```
Thr His Gly Val Phe Leu Leu Asn Ser Asn Gly Met Asp Val Phe Ile
225                 230                 235                 240

Asp Lys Lys Asn Gly Gln Gln Phe Leu Glu Tyr Asn Ile Ile Gly Gly
                245                 250                 255

Val Leu Asp Phe Tyr Phe Val Ala Gly Pro Ser Pro Arg Asp Val Ala
            260                 265                 270

Lys Gln Tyr Ala Glu Ile Thr Thr Leu Pro Leu Met Thr Pro Tyr Trp
        275                 280                 285

Gly Leu Gly Phe His Gln Cys Arg Tyr Gly Tyr Arg Asp Val Tyr Glu
    290                 295                 300

Val Ala Ala Val Val Ala Asn Tyr Ser Ala Ala Gly Ile Pro Leu Glu
305                 310                 315                 320

Thr Met Trp Thr Asp Ile Asp Tyr Met Asp Arg Arg Arg Ile Phe Thr
                325                 330                 335

Ile Asp Pro Glu Arg Phe Pro Ala Asp Lys Tyr Lys Asp Leu Val Asp
                340                 345                 350

Thr Ile His Ala Arg Asp Gln Lys Tyr Ile Val Met Val Asp Pro Ala
            355                 360                 365

Val Tyr Asp Met Glu Ser Asn Pro Ala Leu Asp Ser Gly Leu Glu Tyr
370                 375                 380

Asp Thr Phe Met Lys Glu Pro Asn Gly Ser Asp Tyr Arg Gly Val Val
385                 390                 395                 400

Trp Ala Gly Pro Ser Val Phe Pro Asp Trp Phe Asn Pro Asn Ser Gln
                405                 410                 415

Lys Tyr Trp Asn Glu Leu Phe Ala Asn Phe Phe Asp Gly Glu Asn Gly
                420                 425                 430

Pro Asp Ile Asp Gly Leu Trp Ile Asp Met Asn Glu Pro Ala Asn Phe
            435                 440                 445

Phe Asn Arg Pro Tyr Pro Gly Asn Asn Thr Thr Pro Glu Lys Phe Ala
        450                 455                 460

Glu Ile Asp Gly Asp Pro Pro Lys Pro Pro Val Arg Asp Gly Pro
465                 470                 475                 480

Pro Ala Pro Ile Pro Gly Phe Pro Asp Ser Leu Gln Pro Ala Ser Ser
                485                 490                 495

Arg Leu Asn Thr Arg Glu Ser Val Ser Ile Ala Lys Thr Thr Ile His
            500                 505                 510

Lys Arg Ser Met Ala Ala Arg Thr Thr Ser His Ser Arg Gly Val Gly
        515                 520                 525

Gln Trp Ala Thr Lys Lys His Trp Gly Gln Asn Lys Tyr Gly Arg Pro
    530                 535                 540

Gly Ser Ser Trp Pro Asn Gly Lys Lys Thr Gly Ser Gly Cys Gly Pro
545                 550                 555                 560

Asn Glu Cys Lys Gly Leu Pro Asn Arg Glu Leu Ile Gln Pro Pro Tyr
                565                 570                 575

Met Ile Gln Asn Gly Ala Gly Pro Thr Leu Ala Asp Gly Thr Thr Asp
            580                 585                 590

Thr Asp Leu Val Gln Ser Gly Asp Tyr Leu Gln Tyr Thr His Asn
        595                 600                 605

Leu Tyr Gly Ala Gln Met Ser Thr His Ser His Asn Ala Met Arg Ala
    610                 615                 620

Arg Arg Pro Asp Lys Arg Ala Leu Val Ile Thr Arg Ser Thr Phe Ala
625                 630                 635                 640

Gly Ser Gly Lys Asp Val Ser His Trp Leu Gly Asp Asn Leu Ser Ile
                645                 650                 655
```

```
Trp Asp Gln Tyr Arg Phe Ser Ile Gly Gln Leu Leu Gln Phe Ala Ser
            660                 665                 670

Ile Tyr Gln Ile Pro Val Val Gly Ala Asp Val Cys Gly Phe Gly Gly
        675                 680                 685

Asn Val Thr Glu Thr Leu Cys Ala Arg Trp Ala Thr Leu Gly Ser Phe
690                 695                 700

Tyr Thr Phe Phe Arg Asn His Asn Glu Ile Thr Ala Ala Ser Gln Glu
705                 710                 715                 720

Phe Tyr Arg Trp Pro Lys Val Ala Glu Ala Arg Thr Gly Ile Ala
                725                 730                 735

Ile Arg Tyr Lys Leu Leu Asp Tyr Ile Tyr Thr Ala Ile Tyr Lys Gln
                740                 745                 750

Asn Gln Thr Gly Thr Pro Thr Leu Asn Pro Leu Phe Phe Asn Tyr Pro
            755                 760                 765

Asn Asp Lys Asn Thr Tyr Ser Ile Asp Leu Gln Phe Phe Tyr Gly Asp
770                 775                 780

Gly Ile Leu Val Ser Pro Val Thr Lys Glu Asn Ser Thr Glu Leu Glu
785                 790                 795                 800

Tyr Tyr Leu Pro Asp Asp Ile Phe Tyr Glu Trp Ser Thr Gly Lys Pro
                805                 810                 815

Val Arg Gly Thr Gly Ser Tyr Glu Ser Ala Glu Val Glu Leu Thr Asp
                820                 825                 830

Ile Met Val His Tyr Lys Gly Gly Ile Ile Tyr Pro Gln Arg Val Asp
            835                 840                 845

Ser Ala Asn Thr Thr Ala Leu Arg Lys Lys Gly Phe Asn Leu Val
850                 855                 860

Ile Ala Pro Gly Leu Asn Gly Lys Ala Ser Gly Ser Leu Tyr Leu Asp
865                 870                 875                 880

Asp Gly Glu Ser Val Val Gln Asp Ala Val Ser Glu Ile Asp Phe Thr
                885                 890                 895

Tyr Thr Lys Gly Lys Leu Ser Met Gly Gly Ser Phe Glu Tyr Asp Ala
                900                 905                 910

Gly Val Lys Ile Glu Thr Ile Thr Ile Leu Gly Val Glu Lys Gln Pro
            915                 920                 925

Lys Gly Thr Asp His Ala Glu Tyr Asp Ser Glu Asn Lys Lys Leu Ile
            930                 935                 940

Phe Ala Ala Asp Val Pro Leu Thr Lys Lys Cys Tyr Val Asp Leu Phe
945                 950                 955                 960

<210> SEQ ID NO 3
<211> LENGTH: 27
<212> TYPE: DNA
<213> ORGANISM: Fusarium venenatum

<400> SEQUENCE: 3
gcaggaaaga acaagtgagc aaaaggc                                          27

<210> SEQ ID NO 4
<211> LENGTH: 27
<212> TYPE: DNA
<213> ORGANISM: Fusarium venenatum

<400> SEQUENCE: 4 gcctttttgct cacttgttct ttcctgc                                         27

<210> SEQ ID NO 5
```

-continued

```
<211> LENGTH: 15
<212> TYPE: DNA
<213> ORGANISM: Fusarium venenatum

<400> SEQUENCE: 5
dcctacatgt ttaat                                                    15

<210> SEQ ID NO 6
<211> LENGTH: 13
<212> TYPE: DNA
<213> ORGANISM: Fusarium venenatum

<400> SEQUENCE: 6
dtaaacatgt agg                                                      13

<210> SEQ ID NO 7
<211> LENGTH: 21
<212> TYPE: DNA
<213> ORGANISM: Fusarium venenatum

<400> SEQUENCE: 7
aggcctcacc catctcaaca c                                             21

<210> SEQ ID NO 8
<211> LENGTH: 21
<212> TYPE: DNA
<213> ORGANISM: Fusarium venenatum

<400> SEQUENCE: 8
acatgttggt gatagcagtg a                                             21

<210> SEQ ID NO 9
<211> LENGTH: 36
<212> TYPE: DNA
<213> ORGANISM: Fusarium venenatum

<400> SEQUENCE: 9
cactgctatc accaacatgt tcttcaagaa gctgct                             36

<210> SEQ ID NO 10
<211> LENGTH: 35
<212> TYPE: DNA
<213> ORGANISM: Fusarium venenatum

<400> SEQUENCE: 10
ccaacaaggt atttaattaa tcagaagaga tccac                              35
```